US007901691B2

(12) United States Patent
Tuli et al.

(10) Patent No.: US 7,901,691 B2
(45) Date of Patent: Mar. 8, 2011

(54) CHIMERIC G PROTEIN BASED RABIES VACCINE

(75) Inventors: Rakesh Tuli, Uttar Pradesh (IN); Samir Vishwanath Sawant, Uttar Pradesh (IN); Shadma Ashraf, Uttar Pradesh (IN); Pradhyumna Kumar Singh, Uttar Pradesh (IN); Dinesh Kumar Yadav, Uttar Pradesh (IN); Mohammad Shahnawaz, Uttar Pradesh (IN); Satish Mishra, Uttar Pradesh (IN)

(73) Assignees: Council of Scientific and Indistrial Research, New Delhi (IN); Unichem Laboratories Ltd., Mumbai (IN); Indian Veterinary Research Institute, Izatnagar (IN)

( * ) Notice: Subject to any disclaimer, the term of this patent is extended or adjusted under 35 U.S.C. 154(b) by 1305 days.

(21) Appl. No.: 11/202,864

(22) Filed: Aug. 12, 2005

(65) Prior Publication Data

US 2009/0004215 A1 Jan. 1, 2009

Related U.S. Application Data

(60) Provisional application No. 60/683,054, filed on May 20, 2005.

(30) Foreign Application Priority Data

Aug. 13, 2004 (IN) .......................... 1502/DEL/2004

(51) Int. Cl.
*A61K 39/205* (2006.01)
*C12N 15/00* (2006.01)

(52) U.S. Cl. .................................. 424/224.1; 435/320.1

(58) Field of Classification Search ................ 424/224.1
See application file for complete search history.

(56) References Cited

U.S. PATENT DOCUMENTS

| | | | | |
|---|---|---|---|---|
| 6,673,601 | B1 * | 1/2004 | Jacob et al. | 435/320.1 |
| 7,235,245 | B2 * | 6/2007 | Jacob et al. | 424/224.1 |

FOREIGN PATENT DOCUMENTS

| | | | |
|---|---|---|---|
| WO | WO 95/09249 | A1 * | 4/1995 |
| WO | WO 96/40229 | A1 * | 12/1996 |
| WO | WO 00/63242 | A1 * | 10/2000 |

OTHER PUBLICATIONS

Fu et al. Vaccine. 1993;11(9):925-928.*
Yusibov et al. Vaccine 2002, vol. 20, pp. 3155-3164.*
Lederman et al. Molecular Immunology 1991, vol. 28, No. 11, pp. 1171-1181.*
Jallet et al. (J. Virol. 1999, vol. 73, No. 1, pp. 225-233).*

* cited by examiner

*Primary Examiner* — Robert B Mondesi
*Assistant Examiner* — Bao Li
(74) *Attorney, Agent, or Firm* — Arent Fox LLP

(57) ABSTRACT

A novel chimeric protein of rabies virus designed to express a chimeric G protein at a high level in transgenic plants. A gene was also designed and chemically synthesised to encode the chimeric G protein and expressed at high level in plant tissue. The gene was expressed in transgenic tobacco plants to examine its therapeutic efficacy against infection by rabies virus. The chimeric G protein was enriched in plant membranes. The BalbC mice were immunised with the plant leaf expressed G-protein. Plant derived chimeric G protein elicited higher immune response as compared to the commercial vaccine. The mice displayed protective immunity when they were challenged with live virus. Chimeric G protein expressed at high level in plant leaves was demonstrated to function as a commercially valuable subunit vaccine against rabies virus infection.

27 Claims, 13 Drawing Sheets

Figure 1: Comparison of the gene sequence claimed in this study (chimeric) with that reported in literature (native).

```
Aligned_sequences:
(Seq. ID NO: 2)
Type of sequence : Nucleotides
1: Native (Sequence of ERA patented by Curtis et al., 1983: US Patent
4,393,201)
2: Chimeric
Matrix: EBLOSUM62
Gap_penalty: 10.0
Extend_penalty: 0.5
Length: 1648
Identity:     1187/1648 (72.0%)
Similarity:   1187/1648 (72.0%)
Gaps:           74/1648 ( 4.5%)
Score: 6633.5

Native              1 ATGG--TTCCTCAGGCTCTCCTGTTTGTAC-----CC----CTTCTGGTT
39
                      |||.  |||||||.|..||.|...||.|||     ||    |||| ||..
Chimeric            1 ATGAACTTCCTCAAGTCCTTCCCATTCTACGCATTCCTTTGCTTC-GGAC
49

Native             40 TTTCCATTG-TGTTTTG---------------------------------
55
                      ..|.|.||| ||.|.||
Chimeric           50 AATACTTTGTTGCTGTGACTCATGCTGCACACCACCATCACCACCATATC
99

Native             56 -------GGAAATTCCCTATTTACACGATACTAGACAAGCTTGGTCCCTG
98
                             ||||.||||||||.|||||.||.||.||||||.|.||.||.||
Chimeric          100 GAGGGCAGGAAGTTCCCTATCTACACTATCCTCGACAAGTTGGGCCCTTG
149

Native             99 GAGCCCGATTGACATACATCACCTCAGCTGCCCAAACAATTTGGTAGTGG
148
```

Figure 1 cont.

```
                    1..111.11.11111.11111.111111111111.1111111111.11.1
Chimeric    150 GTCCCCTATCGACATCCATCATCTCAGCTGCCCTAACAATTTGGTTGTCG
199

Native      149 AGGACGAAGGATGCACCAACCTGTCAGGGTTCTCCTACATGGAACTTAAA
198
                    1111111.11.11111.111.1111.11.111..1111111111.11111.
Chimeric    200 AGGACGAGGGCTGCACAAACTTGTCTGGATTCAGCTACATGGAGCTTAAG
249

Native      199 GTTGGATACATCTTAGCCATAAAAATGAACGGGTTCACTTGCACAGGCGT
248
                    11111.111111.1.11.11.11.11111111.11.1111111111111
Chimeric    250 GTTGGCTACATCCTCGCTATCAAGATGAACGGTTTTACTTGCACAGGCGT
299

Native      249 TGTGACGGAGGCTGAAACCTACACTAACTTCGTTGGTTATGTCACAACCA
298
                    .11.11.11111.11.1.111111.11111111.11111.11.11.1111
Chimeric    300 CGTTACTGAGGCCGAGAACTACACCAACTTCGTGGGTTACGTTACTACCA
349

Native      299 CGTTCAAAAGAAAGCATTTCCGCCCAACACCAGATGCATGTAGAGCCGCG
348
                    1.111111.11.111111.11111.11.11.11111.11111..1.11.11.
Chimeric    350 CTTTCAAGAGGAAGCACTTCCGGCCGACTCCAGACGCATGCCGCGCTGCC
399

Native      349 TACAACTGGAAGATGGCCGGTGACCCCAGATATGAAGAGTCTCTACACAA
398
                    111111111111111.111111111..1.11.11.111..11111111
Chimeric    400 TACAACTGGAAGATGGCTGGTGACCCACGTTACGAGGAGAGTCTACACAA
449

Native      399 TCCGTACCCTGACTACCGCTGGCTTCGAACTGTAAAAACCACCAAGGAGT
448
```

Figure 1 cont.

```
                      .||.||||||||||||.|.|||.|.||.||.||.||.||.|||||||
Chimeric              450  CCCATACCCTGACTACAGATGGTTACGTACCGTCAAGACTACTAAGGAGT
499

Native                449  CTCTCGTTATCATATCTCCAAGTGTAGCAGATTTGGACCCATATGACAGA
498

|.|||||.|||||.||.|||...||.||.|||.|.||.|||||.||.||.
Chimeric              500  CCCTCGTCATCATTTCCCCATCCGTGGCCGATCTCGATCCATACGATAGG
549

Native                499  TCCCTTCACTCGAGGGTCTTCCCTAGCGGGAAGTGCTCAGGAGTAGCGGT
548

|||.|.||.||.|||||.|||||...|||.|||||||||.||.||.||.||
Chimeric              550  TCCTTACATTCTAGGGTTTTCCCATCCGGTAAGTGCTCCGGCGTGGCTGT
599

Native                549  GTCTTCTACCTACTGCTCCACTAACCACGATTACACCATTTGGATGCCCG
598

.||.||.||.||||||||||.|||||.||.|||||.||.||||||||.|
Chimeric              600  CTCCTCCACTTACTGCTCCACCAACCATGACTACACTATCTGGATGCCTG
649

Native                599  AGAATCCGAGACTAGGGATGTCTTGTGACATTTTTACCAATAGTAGAGGG
648

||||.||.||...|.||.|||||.||.||.||.||.||......||||.
Chimeric              650  AGAACCCTAGGTTGGGTATGTCCTGCGATATCTTCACTAACTCGCGAGGT
699

Native                649  AAGAGAGCATCCAAAGGGAGTGAGACTTGCGGCTTTGTAGATGAAAGAGG
698

|||||.||...|||.||....|||||.|||||.||.||.|||||.||||
Chimeric              700  AAGAGGGCCAGCAAGGGTTCCGAGACCTGCGGTTTCGTCGATGAGAGAGG
749

Native                699  CCTATATAAGTCTTTAAAAGGAGCATGCAAACTCAAGTTATGTGGAGTTC
748

```
Chimeric    750 TTTGTACAAGTCCCTCAAGGGCGCCTGCAAGCTCAAGTTGTGCGGTGTCC
799

Native      749 TAGGACTTAGACTTATGGATGGAACATGGGTCGCGATGCAAACATCAAAT
798

|.||.|||||..|.|||||.||.||.|||||||||.||||||||....||.
Chimeric    800 TCGGTCTTAGGTTGATGGACGGTACCTGGGTCGCTATGCAAACTAGTAAC
849

Native      799 GAAACCAAATGGTGCCCTCCCGATCAGTTGGTGAACCTGCACGACTTTCG
848

||.||.||.|||||||||.||.||.||.|||||.|||||.||||||||.||
Chimeric    850 GAGACTAAGTGGTGCCCACCAGACCAATTGGTCAACCTCCACGACTTCCG
899

Native      849 CTCAGACGAAATTGAGCACCTTGTTGTAGAGGAGTTGGTCAGGAAGAGAG
898

.||.|||||.||.||||||.|.||.||.|||||...|.||.||||||||.|
Chimeric    900 GTCCGACGAGATCGAGCACTTGGTCGTGGAGGAACTCGTTAGGAAGAGGG
949

Native      899 AGGAGTGTCTGGATGCACTAGAGTCCATCATGACAACCAAGTCAGTGAGT
948

||||.||..|||||||.||.|||||||||.|||||.||.|||||.||...|
Chimeric    950 AGGAATGCTTGGATGCTCTCGAGTCCATTATGACTACTAAGTCCGTCTCT
999

Native      949 TTCAGACGTCTCAGTCATTTAAGAAAACTTGTCCCTGGGTTTGGAAAAGC
998

||||||.|.|||||.|||.|.||.||..|.||.||.||.||.||.||.||
Chimeric   1000 TTCAGAAGGCTCAGCCATCTCAGGAAGTTGGTTCCAGGTTTCGGCAAGGC
1049

Native      999 ATATACCATATTCAACAAGACCTTGATGGAAGCCGATGCTCACTACAAGT
1048

```
Chimeric      1050 CTATACCATTTTCAACAAGACTTTGATGGAGGCTGACGCTCACTACAAGT
1099

Native        1049 CAGTCAGAACTTGGAATGAGATCCTCCCTTCAAAAGGGTGTTTAAGAGTT
1098
                   |.|||.|.||.|||||.||||||||||.||.||.||.||...|.||.|||
Chimeric      1100 CCGTCCGGACCTGGAACGAGATCCTCCCATCCAAGGGCTGCCTTAGGGTT
1149

Native        1099 GGGGGGAGGTGTCATCCTCATGTGAACGGGGTGTTTTTCAATGGTATAAT
1148
                   ||.||..|.||.|||||.||.||.|||||.||.||||||||.||.||.||
Chimeric      1150 GGCGGCCGCTGCCATCCACACGTTAACGGTGTCTTTTTCAACGGCATTAT
1199

Native        1149 ATTAGGACCTGACGGCAATGTCTTAATCCCAGAGATGCAATCATCCCTCC
1198
                   ..|.||.||.|||||||||.||.||.||||||||||||||.||.||||||.
Chimeric      1200 CCTCGGCCCCGACGGCAACGTTTTGATCCCAGAGATGCAGTCCTCCCTCT
1249

Native        1199 TCCAGCAACATATGGAGTTGTTGGAATCCTCGGTTATCCCCCTTGTGCAC
1248
                   |.|||||.||.|||||||||.|.|||..|||.||||||||..|.||.||.
Chimeric      1250 TGCAGCAGCACATGGAGTTGCTCGAAAGCTCTGTTATCCCATTGGTCCAT
1299

Native        1249 CCCCTGGCAGACCCGTCTACCGTTTTCAAGGACGGTGACGAGGCTGAGGA
1298
                   ||..||||.|||||.||.||.||.|||||||||.||.||||||||.|||||
Chimeric      1300 CCATTGGCTGACCCTTCCACTGTCTTCAAGGATGGCGACGAGGCCGAGGA
1349

Native        1299 TTTTGTTGAAGTTCACCTTCCCGATGTGCACAATCAGGTCTCAGGAGTTG
1348
                   .||.||.||.||.||.||...|.||.||.||.|||||.|||||.||.||||||.|
```

Figure 1 cont.

```
Chimeric    1350 CTTCGTGGAGGTGCATTTGCCAGACGTTCACAACCAGGTTTCCGGAGTGG
1399

Native      1349 ACTTGGGTCTCCCGAACTGGGGGAAGTATGTATTACTGAGTGCAGGGGCC
1398
                 ||.|.|||||||||.|||||||.|||||.||.||.||....|||||.||.
Chimeric    1400 ACCTCGGTCTCCCAAACTGGGGTAAGTACGTCTTGCTCTCCGCAGGCGCG
1449

Native      1399 CTGACTGCCTTGATGTTGATAATTTTCCTGATGACATGTTGTAGAAGAGT
1448
                 ||.||||||||||||||||||||.||.|||||.|||||.||.||.||||.||
Chimeric    1450 CTCACTGCCTTGATGTTGATCATCTTCCTCATGACTTGCTGCAGAAGGGT
1499

Native      1449 CAATCGATCAGAACCTACGCAACACAATCTCAGAGGGACAGGGAGGGAGG
1498
                 |||..|.||.||.||.||.||.||.||..|.||.||.||.||.|||||||
Chimeric    1500 CAACAGGTCCGAGCCAACTCAGCATAACTTGAGGGGCACCGGTAGGGAGG
1549

Native      1499 TGTCAGTCACTCCCCAAAGCGGGAAGATCATATCTTCATGGAATCACAC
1548
                 |.||.||.|||||.||...|||.|||||.|||||.||.|||||.||.||.
Chimeric    1550 TCTCCGTTACTCCACAGTCCGGAAAGATTATATCCTCTTGGGAGTCCCAT
1599

Native      1549 AAGAGTGGGGGTGAGAC-C---AGACTGTGA
1575
                 |||...||.||.|||||  .|.|.|.||
Chimeric    1600 AAGTCCGGAGGCGAGACGCGTTTGTCCGAGAAGGATGAGTTGTGATGA
1647
```

Figure 2: Comparison of the amino acid sequence claimed in this study (chimeric) with that reported in literature (native).

Aligned_sequences:

(Seq. ID NO: 1)
Type of sequence :Amino acid
1: CHIMERIC
2: NATIVE
Matrix         : EBLOSUM62
Gap_penalty    : 10.0
Extend_penalty : 0.5
Length: 550
Identity           : 511/550 (92.9 %)
Similarity     : 511/550 (92.9 %)
Gaps           : 29/550 ( 5.3%)
Score: 2710.5

```
CHIMERIC     1    MNFLKSFPFYAF-LCFGQYFVAVTHAAHHHHHHIEGRKFPIYTILDKL
47
                   ...!...!...! !!!!                 !!!!!!!!!!!!
NATIVE       1    MVPQALLFVPLLVFPLCFG------------------KFPIYTILDKL
30

CHIMERIC     48   GPWSPIDIHHLSCPNNLVVEDEGCTNLSGFSYMELKVGYILAIKMNGFTC
97
                  !!!!!!!!!!!!!!!!!!!!!!!!!!!!!!!!!!!!!!!!!!!!!!!!!
NATIVE       31   GPWSPIDIHHLSCPNNLVVEDEGCTNLSGFSYMELKVGYILAIKMNGFTC
80

CHIMERIC     98   TGVVTEAENYTNFVGYVTTTFKRKHFRPTPDACRAAYNWKMAGDPRYEES
147
                  !!!!!!!!.!!!!!!!!!!!!!!!!!!!!!!!!!!!!!!!!!!!!!!!!
NATIVE       81   TGVVTEAETYTNFVGYVTTTFKRKHFRPTPDACRAAYNWKMAGDPRYEES
130
```

Figure 2 cont.

```
CHIMERIC    148  LHNPYPDYRWLRTVKTTKESLVIISPSVADLDPYDRSLHSRVFPSGKCSG
197
                 |||||||||||||||||||||||||||||||||||||||||||||||||
NATIVE      131  LHNPYPDYRWLRTVKTTKESLVIISPSVADLDPYDRSLHSRVFPSGKCSG
180

CHIMERIC    198  VAVSSTYCSTNHDYTIWMPENPRLGMSCDIFTNSRGKRASKGSETCGFVD
247
                 |||||||||||||||||||||||||||||||||||||||||||||||||
NATIVE      181  VAVSSTYCSTNHDYTIWMPENPRLGMSCDIFTNSRGKRASKGSETCGFVD
230

CHIMERIC    248  ERGLYKSLKGACKLKLCGVLGLRLMDGTWVAMQTSNETKWCPPDQLVNLH
297
                 |||||||||||||||||||||||||||||||||||||||||||||||||
NATIVE      231  ERGLYKSLKGACKLKLCGVLGLRLMDGTWVAMQTSNETKWCPPDQLVNLH
280

CHIMERIC    298  DFRSDEIEHLVVEELVRKREECLDALESIMTTKSVSFRRLSHLRKLVPGF
347
                 |||||||||||||||||||||||||||||||||||||||||||||||||
NATIVE      281  DFRSDEIEHLVVEELVRKREECLDALESIMTTKSVSFRRLSHLRKLVPGF
330

CHIMERIC    348  GKAYTIFNKTLMEADAHYKSVRTWNEILPSKGCLRVGGRCHPHVNGVFFN
397
                 |||||||||||||||||||||||||||||||||||||||||||||||||
NATIVE      331  GKAYTIFNKTLMEADAHYKSVRTWNEILPSKGCLRVGGRCHPHVNGVFFN
380

CHIMERIC    398  GIILGPDGNVLIPEMQSSLLQQHMELLESSVIPLVHPLADPSTVFKDGDE
447
                 |||||||||||||||||||||||||||||||||||||||||||||||||
NATIVE      381  GIILGPDGNVLIPEMQSSLLQQHMELLESSVIPLVHPLADPSTVFKDGDE
430
```

Figure 2 cont.

```
CHIMERIC      448  AEDFVEVHLPDVHNQVSGVDLGLPNWGKYVLLSAGALTALMLIIFLMTCC
497
                   |||||||||||||||||||||||||||||||||||||||||||||||||
NATIVE        431  AEDFVEVHLPDVHNQVSGVDLGLPNWGKYVLLSAGALTALMLIIFLMTCC
480

CHIMERIC      498  RRVNRSEPTQHNLRGTGREVSVTPQSGKIISSWESHKSGGETRLSEKDEL
547
                   |||||||||||||||||||||||||||||||||||||||||||
NATIVE             481  RRVNRSEPTQHNLRGTGREVSVTPQSGKIISSWESHKSGGETRL
524
```

Figure 3

Synthetic novel chimeric G - protein gene in cloning vector, used for the construction of *E. coli* plant expression vector

*Hind* III — PR-S-(His)$_6$-Xa-G-Protein-SEKDEL — *Sac* I pSA17

- lacZ
- f$_1$(+) origin
- ColE 1 origin
- bl Ampicillin

E.coli expression cassette used for expressing the chimeric protein in *E. coli*, using the synthetic chimeric gene Plant expression cassette used for developing transgenic plants in this study

Figure 6

*Anti-rabies immuneresponse in Balb/c mice injected intraperitoneally with rabies virus glycoprotein.*

Figure 7

*Immunoprotection of Balb/c mice after intracerebral challenge with live rabies virus.*

SEQUENCE LISTING

```
<160> NUMBER OF SEQ ID NOS: 65

<210> SEQ ID NO 1
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asn Phe Leu Lys Ser Phe Pro Phe Tyr Ala Phe Leu Cys Phe Gly
1               5                   10                  15

Gln Tyr Phe Val Ala Val Thr His Ala Ala His His His His His His
                20                  25                  30

Ile Glu Gly Arg Lys Phe Pro Ile Tyr Thr Ile Leu Asp Lys Leu Gly
            35                  40                  45

Pro Trp Ser Pro Ile Asp Ile His His Leu Ser Cys Pro Asn Asn Leu
    50                  55                  60

Val Val Glu Asp Glu Gly Cys Thr Asn Leu Ser Gly Phe Ser Tyr Met
65                  70                  75                  80

Glu Leu Lys Val Gly Tyr Ile Leu Ala Ile Lys Met Asn Gly Phe Thr
                85                  90                  95

Cys Thr Gly Val Val Thr Glu Ala Glu Asn Tyr Thr Asn Phe Val Gly
            100                 105                 110

Tyr Val Thr Thr Thr Phe Lys Arg Lys His Phe Arg Pro Thr Pro Asp
            115                 120                 125

Ala Cys Arg Ala Ala Tyr Asn Trp Lys Met Ala Gly Asp Pro Arg Tyr
        130                 135                 140

Glu Glu Ser Leu His Asn Pro Tyr Pro Asp Tyr Arg Trp Leu Arg Thr
145                 150                 155                 160

Val Lys Thr Thr Lys Glu Ser Leu Val Ile Ile Ser Pro Ser Val Ala
                165                 170                 175

Asp Leu Asp Pro Tyr Asp Arg Ser Leu His Ser Arg Val Phe Pro Ser
            180                 185                 190

Gly Lys Cys Ser Gly Val Ala Val Ser Ser Thr Tyr Cys Ser Thr Asn
        195                 200                 205

His Asp Tyr Thr Ile Trp Met Pro Glu Asn Pro Arg Leu Gly Met Ser
    210                 215                 220

Cys Asp Ile Phe Thr Asn Ser Arg Gly Lys Arg Ala Ser Lys Gly Ser
225                 230                 235                 240

Glu Thr Cys Gly Phe Val Asp Glu Arg Gly Leu Tyr Lys Ser Leu Lys
                245                 250                 255
```

```
Gly Ala Cys Lys Leu Lys Leu Cys Gly Val Leu Gly Leu Arg Leu Met
            260                 265                 270

Asp Gly Thr Trp Val Ala Met Gln Thr Ser Asn Glu Thr Lys Trp Cys
        275                 280                 285

Pro Pro Asp Gln Leu Val Asn Leu His Asp Phe Arg Ser Asp Glu Ile
    290                 295                 300

Glu His Leu Val Val Glu Leu Val Arg Lys Arg Glu Glu Cys Leu
305                 310                 315                 320

Asp Ala Leu Glu Ser Ile Met Thr Thr Lys Ser Val Ser Phe Arg Arg
                325                 330                 335

Leu Ser His Leu Arg Lys Leu Val Pro Gly Phe Gly Lys Ala Tyr Thr
            340                 345                 350

Ile Phe Asn Lys Thr Leu Met Glu Ala Asp Ala His Tyr Lys Ser Val
        355                 360                 365

Arg Thr Trp Asn Glu Ile Leu Pro Ser Lys Gly Cys Leu Arg Val Gly
    370                 375                 380

Gly Arg Cys His Pro His Val Asn Gly Val Phe Phe Asn Gly Ile Ile
385                 390                 395                 400

Leu Gly Pro Asp Gly Asn Val Leu Ile Pro Glu Met Gln Ser Ser Leu
                405                 410                 415

Leu Gln Gln His Met Glu Leu Leu Glu Ser Ser Val Ile Pro Leu Val
            420                 425                 430

His Pro Leu Ala Asp Pro Ser Thr Val Phe Lys Asp Gly Asp Glu Ala
        435                 440                 445

Glu Asp Phe Val Glu Val His Leu Pro Asp Val His Asn Gln Val Ser
    450                 455                 460

Gly Val Asp Leu Gly Leu Pro Asn Trp Gly Lys Tyr Val Leu Leu Ser
465                 470                 475                 480

Ala Gly Ala Leu Thr Ala Leu Met Leu Ile Ile Phe Leu Met Thr Cys
                485                 490                 495

Cys Arg Arg Val Asn Arg Ser Glu Pro Thr Gln His Asn Leu Arg Gly
            500                 505                 510

Thr Gly Arg Glu Val Ser Val Thr Pro Gln Ser Gly Lys Ile Ile Ser
        515                 520                 525

Ser Trp Glu Ser His Lys Ser Gly Gly Glu Thr Arg Leu Ser Glu Lys
    530                 535                 540

Asp Glu Leu
545

<210> SEQ ID NO 2
<211> LENGTH: 1647
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
atgaacttcc tcaagtcctt cccattctac gcattccttt gcttcggaca atactttgtt      60
gctgtgactc atgctgcaca ccaccatcac caccatatcg agggcaggaa gttccctatc     120
tacactatcc tcgacaagtt gggcccttgg tccctatcg acatccatca tctcagctgc      180
cctaacaatt tggttgtcga ggacgagggc tgcacaaact tgtctggatt cagctacatg     240
gagcttaagg ttggctacat cctcgctatc aagatgaacg ttttacttg cacaggcgtc     300 gttactgagg ccgagaacta caccaacttc gtgggttacg ttactaccac tttcaagagg     360
```

```
aagcacttcc ggccgactcc agacgcatgc cgcgctgcct acaactggaa gatggctggt    420
gacccacgtt acgaggagag tctacacaac ccatacccctg actacagatg gttacgtacc   480
gtcaagacta ctaaggagtc cctcgtcatc atttccccat ccgtggccga tctcgatcca    540
tacgataggt ccttacattc tagggttttc ccatccggta agtgctccgg cgtggctgtc    600
tcctccactt actgctccac caaccatgac tacactatct ggatgcctga aaccctagg    660 ttgggtatgt cctgcgatat cttcactaac tcgcgaggta agagggccag caagggttcc    720
gagacctgcg gtttcgtcga tgagagaggt ttgtacaagt ccctcaaggg cgcctgcaag    780
ctcaagttgt gcggtgtcct cggtcttagg ttgatggacg gtacctgggt cgctatgcaa    840
actagtaacg agactaagtg gtgcccacca gaccaattgg tcaacctcca cgacttccgg    900
tccgacgaga tcgagcactt ggtcgtggag aactcgtta ggaagaggga ggaatgcttg     960
gatgctctcg agtccattat gactactaag tccgtctctt tcagaaggct cagccatctc   1020
aggaagttgg ttccaggttt cggcaaggcc tataccattt tcaacaagac tttgatggag   1080
gctgacgctc actacaagtc cgtccggacc tggaacgaga tcctcccatc caagggctgc   1140 cttaggttg gcggccgctg ccatccacac gttaacggtg tcttttcaa cggcattatc    1200 ctcggccccg acggcaacgt tttgatccca gagatgcagt cctccctctt gcagcagcac   1260
atggagttgc tcgaaagctc tgttatccca ttggtccatc cattggctga ccttccact   1320 gtcttcaagg atggcgacga ggccgaggac ttcgtggagg tgcatttgcc agacgttcac   1380
aaccaggttt ccggagtgga cctcggtctc ccaaactggg gtaagtacgt cttgctctcc   1440
gcaggcgcgc tcactgcctt gatgttgatc atcttcctca tgacttgctg cagaagggtc   1500
aacaggtccg agccaactca gcataacttg agggggcaccg gtagggaggt ctccgttact   1560
ccacagtccg gaaagattat atcctcttgg gagtcccata agtccggagg cgagacgcgt   1620
ttgtccgaga aggatgagtt gtgatga                                      1647
```

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaagctttc tagataaaca atgaacttcc tcaagtcatt c                        41

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcctttgctt cggacaatac tttgttgctg tgac                                34

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccatcaccac catatcgagg gaaggaagtt ccctatctac                                  40

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcgacaagt tgggcccttg gtccctatc gacatccatc atctcagc                          48

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcgaggacg agggctgcac aaacttgtct ggattcagct acatggagc                       49

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catcctcgct atcaagatga acggttttac ttgcacaggc gtcgttac                        48

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaacttcgt gggttacgtt actaccactt tcaagaggaa gcacttcc                        48

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgcgctgcc tacaactgga agatggctgg tgacccacgt tacgagg                         47

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taccctgact acagatggtt acgtaccgtc aagactacta aggagtc                         47

```
<210> SEQ ID NO 12
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atccgtggcc gatctcgatc catactcctc agggagcagt agtaaagggg taggcaccgg    60
ctagg                                                                65

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctccggcgtg gctgtctcct ccacttactg ctccaccaac catgactaca              50

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaaccctagg ttgggtatgt cctgcgatat cttcactaac tcgcgagg                48

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttccgagacc tgcggtttcg tcgatgagag aggtttgtac aagtccctc               49

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caagttgtgc ggtgtcctcg gtcttaggtt gatggacggt acctgggt                48

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agactaagtg gtgcccacca gaccaattgg tcaacctcca cgacttccgg tccgacga     58
```

-continued

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tggtcgtgga ggaactcgtt aggaagaggg aggaatgctt ggatgc         46

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gactactaag tccgtctctt tcagaaggct cagccatctc aggaag         46

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ggcctatacc attttcaaca agactttgat ggaggctgac gctcact        47

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
tggaacgaga tcctcccatc caagggctgc cttagggttg gcggccgctg c    51

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gtcttttcta acggcattat cctcggcccc gacggcaacg ttttgatcc       49

<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
tcttgcagca gcacatggag ttgctcgaaa gctctgttat cccattggtc ca   52

```
<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgacccttcc actgtcttca aggatggcga cgaggccgag gacttcgtg                49

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgttcacaac caggtttccg gagtggacct cggtctccca aactggggta               50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgcaggcgcg ctcactgcct tgatgttgat catcttcctc atgacttgct               50

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aggtccgagc caactcagca taacttgagg ggcaccggta gggaggtc                 48

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tccggaaaga ttatatcctc ttgggagtcc cataagtccg gaggcgagac               50

<210> SEQ ID NO 29
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgggatccaa gcttgagctc tcatcacaac tcatccttct cggacaaacg cgtctcgcct   60
ccggacttat ggga                                                     74
```

```
<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatataatct ttccggactg tggagtaacg gagacctccc taccggt            47

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agttggctcg gacctgttga cccttctgca gcaagtcatg aggaagat            48

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgagcgcgcc tgcggagagc aagacgtact taccccagtt tgggaga            47

<210> SEQ ID NO 33
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aacctggttg tgaacgtctg gcaaatgcac ctccacgaag tcctcggcc            49

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agacagtgga agggtcagcc aatggatgga ccaatgggat aacagagc            48

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctgctgcaag agggaggact gcatctctgg gatcaaaacg ttgccgt            47

<210> SEQ ID NO 36
<211> LENGTH: 51
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atgccgttga aaagacacc gttaacgtgt ggatggcagc ggccgccaac c            51

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaggatctc gttccaggtc cggacggact tgtagtgagc gtcagcc                47

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaaaatggta taggccttgc cgaaacctgg aaccaacttc ctgagatggc             50

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gacggactta gtagtcataa tggactcgag agcatccaag cattcctccc             50

<210> SEQ ID NO 40
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttcctccacg accaagtgct cgatctcgtc ggaccggaag tcgtggaggt tgaccaat    58

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caccacttag tctcgttact agtttgcata gcgacccagg taccgtc                47

<210> SEQ ID NO 42
<211> LENGTH: 49
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 42
gacaccgcac aacttgagct tgcaggcgcc cttgagggac ttgtacaaa                    49

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcaggtctcg gaaccttgc tggccctctt acctcgcgag ttagtga                       47

<210> SEQ ID NO 44
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acccaaccta gggttctcag gcatccagat agtgtagtca tggttggtg                    49

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cagccacgcc ggagcactta ccggatggga aaaccctaga atgtaaggac                   50

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gatcggccac ggatggggaa atgatgacga gggactcctt agtagt                       46

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
catctgtagt cagggtatgg gttgtgtaga ctctcctcgt aacgtggg                     48

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 48
gtaggcagcg cggcatgcgt ctggagtcgg ccggaagtgc ttcctctt          48

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aacgtaaccc acgaagttgg tgtagttctc ggcctcagta acgacgcctg tgc          53

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttgatagcga ggatgtagcc aaccttaagc tccatgtagc tgaat          45

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccctcgtcct cgacaaccaa attgttaggg cagctgagat gatggatgt          49

<210> SEQ ID NO 52
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccaagggccc aacttgtcga ggatagtgta gatagggaac ttcc          44

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atatggtggt gatggtggtg tgcagcatga gtcacagcaa caaag          45

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 54
gcaaaggaat gcgtagaatg ggaatgactt gaggaagttc                           40

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Asp Asp Asp Lys
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Val Pro Arg Gly Ser
1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Glu Glu Arg
1

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Glu Lys Asp Glu Leu
1               5

<210> SEQ ID NO 60
<211> LENGTH: 12
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 60
taaacaatga ac                                                          12

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Glu Gly Arg
1

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 62

His His His His His His His His His His
1               5                   10

<210> SEQ ID NO 63
<211> LENGTH: 1575
<212> TYPE: DNA
<213> ORGANISM: Rabies virus

<400> SEQUENCE: 63
atggttcctc aggctctcct gtttgtaccc cttctggttt ttccattgtg ttttgggaaa      60
ttccctattt acacgatact agacaagctt ggtccctgga gcccgattga catacatcac 120
ctcagctgcc caaacaattt ggtagtggag gacgaaggat gcaccaacct gtcagggttc 180
tcctacatgg aacttaaagt tggatacatc ttagccataa aaatgaacgg gttcacttgc 240
acaggcgttg tgacggaggc tgaaacctac actaacttcg ttggttatgt cacaaccacg 300
ttcaaaagaa agcatttccg cccaacacca gatgcatgta gagccgcgta caactggaag 360
atggccggtg accccagata tgaagagtct ctacacaatc cgtaccctga ctaccgctgg 420
cttcgaactg taaaaaccac caaggagtct ctcgttatca tatctccaag tgtagcagat 480
ttggacccat atgacagatc ccttcactcg agggtcttcc ctagcgggaa gtgctcagga 540
gtagcggtgt cttctaccta ctgctccact aaccacgatt acaccatttg gatgcccgag 600
aatccgagac tagggatgtc ttgtgacatt tttaccaata gtagagggaa gagagcatcc 660
aaagggagtg agacttgcgg ctttgtagat gaaagaggcc tatataagtc tttaaaagga 720
gcatgcaaac tcaagttatg tggagttcta ggacttagac ttatggatgg aacatgggtc 780
gcgatgcaaa catcaaatga aaccaaatgg tgccctcccg atcagttggt gaacctgcac 840
gactttcgct cagacgaaat tgagcacctt gttgtagagg agttggtcag gaagagagag 900
gagtgtctgg atgcactaga gtccatcatg acaaccaagt cagtgagttt cagacgtctc 960
agtcatttaa gaaaacttgt ccctgggttt ggaaaagcat ataccatatt caacaagacc 1020
ttgatggaag ccgatgctca ctacaagtca gtcagaactt ggaatgagat cctcccttca 1080
aaagggtgtt taagagttgg ggggaggtgt catcctcatg tgaacggggt gtttttcaat 1140

```
ggtataatat taggacctga cggcaatgtc ttaatcccag agatgcaatc atccctcctc    1200
cagcaacata tggagttgtt ggaatcctcg gttatccccc ttgtgcaccc cctggcagac    1260
ccgtctaccg ttttcaagga cggtgacgag gctgaggatt tgttgaagt tcaccttccc     1320
```
*(line 1320 as visible)*
```
gatgtgcaca atcaggtctc aggagttgac ttgggtctcc cgaactgggg gaagtatgta    1380
ttactgagtg caggggccct gactgccttg atgttgataa ttttcctgat gacatgttgt    1440
agaagagtca atcgatcaga acctacgcaa cacaatctca gagggacagg gagggaggtg    1500
tcagtcactc cccaaagcgg gaagatcata tcttcatggg aatcacacaa gagtgggggt    1560
gagaccagac tgtga                                                     1575

<210> SEQ ID NO 64
<211> LENGTH: 524
<212> TYPE: PRT
<213> ORGANISM: Rabies virus

<400> SEQUENCE: 64

Met Val Pro Gln Ala Leu Leu Phe Val Pro Leu Leu Val Phe Pro Leu
1               5                   10                  15

Cys Phe Gly Lys Phe Pro Ile Tyr Thr Ile Leu Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
```

```
                    290                 295                 300
Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                    325                 330                 335

Phe Asn Lys Thr Leu Met Glu Ala Asp Ala His Tyr Lys Ser Val Arg
                    340                 345                 350

Thr Trp Asn Glu Ile Leu Pro Ser Lys Gly Cys Leu Arg Val Gly Gly
                355                 360                 365

Arg Cys His Pro His Val Asn Gly Val Phe Phe Asn Gly Ile Ile Leu
            370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                    405                 410                 415

Pro Leu Ala Asp Pro Ser Thr Val Phe Lys Asp Gly Asp Glu Ala Glu
                420                 425                 430

Asp Phe Val Glu Val His Leu Pro Asp Val His Asn Gln Val Ser Gly
            435                 440                 445

Val Asp Leu Gly Leu Pro Asn Trp Gly Lys Tyr Val Leu Leu Ser Ala
        450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                    485                 490                 495

Gly Arg Glu Val Ser Val Thr Pro Gln Ser Gly Lys Ile Ile Ser Ser
                500                 505                 510

Trp Glu Ser His Lys Ser Gly Gly Glu Thr Arg Leu
                515                 520

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Gly His His His His His His His His His
1               5                   10
```

CHIMERIC G PROTEIN BASED RABIES VACCINE

CROSS REFERENCE TO RELATED APPLICATION

The present application claims benefit under 35 U.S.C. §119 to U.S. provisional application No. 60/683,054 filed on May 20, 2005 and also claims benefit under 35 U.S.C. §119 to Indian Patent Application No. 1502/DEL/2004 filed on Aug. 13, 2004. The disclosures of which are hereby incorporated by reference in their entirety.

FIELD OF INVENTION

The present invention relates to a recombinant chimeric G-protein based rabies vaccine having SEQ ID No. 1 and its parts or variants thereof expressed in plant tissue. The invention also relates to a chimeric gene of SEQ ID No. 2 that encodes a chimeric G-protein based rabies vaccine having SEQ ID No 1. The invention also provides a method for large scale production of the chimeric G protein based rabies vaccine and a method of vaccinating a subject for rabies.

BACKGROUND

Reference may be made to WHO, 1989, WHO expert committee on Rabies: WHO Technical Report, WHO, Geneva reporting that rabies is one of the most important and widespread zoonotic diseases and is, with the exception of a few countries, a truly global problem. Rabies is a dreadful disease, one of the oldest known to mankind. It spreads due to the bite of an infected animal or by mucosal exposure. Once the symptoms appear, it proves fatal.

Reference may be made to Hohnes et al., 2002; "Genetic Constraints and the Adaptive Evolution of Rabies Virus in Nature" Virology 292, 247-257 who used a molecular evolutionary approach to investigate the adaptation of rabies virus in nature. Their analysis revealed that the DNA sequence of the nucleoprotein (N) and glycoprotein (G) genes of natural viral isolates were highly constrained, especially at nonsynonymous sites, in contrast to the higher rates of nonsynonymous evolution observed in viruses subject to laboratory passage. In evidence to this statement Charlton et al., 1997. "The long incubation period in rabies: Delayed progression of infection in muscle at the site of exposure", Acta Neuropathologica. 94, 73-77 reported that although rabies virus has a strong neurotropism, replication in vivo does not take place only in neuronal cells. In particular, the virus replicates in muscle tissue also at the site of inoculation before entering the peripheral and central nervous system as well as the salivary gland and other non nervous tissues. Such a process has been documented by Morimoto et al., 1996. "Characterization of a unique variant of bat rabies virus responsible for newly emerging human cases in North America" Proc. Natl. Acad. Sci. USA 93, 5653-5658 who state that in vitro substitutions in the viral glycoprotein (G) sequence accumulate in cell culture of rabies virus and change the tropism for nervous tissues, thereby changing virulence. This shows an adaptive process of virus which was also highlighted in study of Kissi et al., 1999 "Dynamics of rabies virus quasispecies during serial passages in heterologous hosts", J. Gen. Virol. 80, 2041-2050 who observed substantial genetic variation in the G protein coding gene from viruses passaged through different host species.

Reference may be made to Patrick et al., 1987. U.S. Pat. No. 4,707,356 wherein, a peptide vaccine requires identifying an antigenic determinant on the virus which has a sequence that is highly conserved among the various strains. A segment of the rabies virus coat glycoprotein was discovered which has a sequence homologous with the conserved sequence of the segment of the curaremimetic, snake—venom neurotoxins which includes the segment through which the toxins are thought to bind to the acetylcholine receptor binding—site (the AchR) at neuromuscular junctions. Lentz et al. reported in Science 226, 847-848 (1984) "Amino acid sequence similarity between rabies virus glycoprotein and snake venom curaremimetic neurotoxins" that rabies virus accumulates at the neuromuscular junction by binding to the acetylcholine receptors at such junction. Findings reported by Lenz et al. are that the binding of rabies virus at the neuromuscular junction can be blocked by pre-incubation of tissue including such junctions with the curaremimetic, snake—venom neurotoxin, alpha—bungarotoxin, which is known to bind tightly to the acetylcholine (Ach) binding site of the AchR.

Reference may be made to Dietzschold et al., 1979. "Rabies virus strain. A comparative study by polypeptide analysis of vaccine strain with different pathogenic patterns" Virology 98 63-75 wherein five constituent polypeptides of the rabies vaccine virus strains ERA, HEP, CVS and PM (Stereotype I) and Mokola (Serotype 3) were examined by tryptic peptide analysis and revealed general similarity between the nucleoproteins of Mokola and four serotype 1 strains while overall comparison of the tryptic vaccine strains indicates that CVS and PM are more closely related to each other than to ERA or HEP.

Reference may be made to Slater Aug. 9, 1977 U.S. Pat. No. 4,040,904 "Novel rabies virus vaccine and processes" wherein, the ERA strain of the rabies virus was derived from SAD virus strain, originally isolated from a rabid dog and propagated in mouse brain and hamster kidney cells and then adapted to primary pig kidney tissue culture. A sample of the ERA strain of rabies virus was deposited with the American Type Culture Collection, Washington, D.C. on Oct. 29, 1964 and was recorded there as number VR 332. Vaccines containing the ERA strain adapted to primary pig kidney tissue culture are widely used in immunizing various animal species including dogs, cats and cattle against rabies. According to the invention, an improved attenuated strain of rabies virus having a significantly reproducible cytopathic activity is provided. The improved rabies virus strain used in this invention is prepared from the ERA strain of rabies virus. The ERA rabies strain has been identified by Abelseth, M. K. in "Propagation of Rabies virus in Pig Kidney Cell Culture", Can. Vet. J. 584-87 (1964) and Abelseth, M. G., "An Attenuated Rabies Vaccine for Domestic Animals Produced in Tissue Culture", Can. Vet. J. 5279-286 (1964) was derived from the rabies virus described by Fenje, P., in "Propagation of Rabies Virus in Cultures of Hamster Kidney Cells". Can J. Microbiol, 6 379-484.

Reference may be made to Thoulouze et al., 1997, "Rabies virus infects mouse and human lymphocytes and induces apoptosis" in Journal of Virology 71: 10: 7372-7380, who showed that the rabies virus infects both mouse spleen lymphocytes and the human T-lymphocyte cell line. Jurkat found that attenuated rabies virus strain ERA infects ConA-activated splenocytes and T-cell lines more efficiently than CVS which is a highly neurovirulent rabies virus strain and reported that in contrast to CVS, ERA rabies virus and other attenuated viruses stimulate a strong immune response and can be efficient live vaccines. Both inactivated and attenuated viruses are used for immunization but the cost of production of inactivated virus is a major problem. Secondly, such a vaccine should be completely inactivated and for such purposes it is pre-requisite that candidate vaccine should be avirulent strain of the virus but it should be immunogenic and genetically stable. (Hooper et al., 1998, Collaboration of antibody and inflammation in the clearance of rabies virus from the CNS" in Journal of Virology; 72: 3711-9).

Yang et al., 1992 in Journal of General Virology; 73: 895-900, "Basis of neurovirulent rabies virus variant Av01 with sterotaxic brain inoculation in mice" reported that pathogenicity is not only a function of the virus but is also largely dependent on the site of infection and the immune status of the host. Even the most attenuated rabies viruses can potentially cause a lethal encephalomyelitis, which suggests that even inactivated and attenuated viruses are not reliable source for vaccination.

Reference may be made to Coslett et al., 1980, "The structural proteins of rabies virus and evidence for their synthesis from separate monocistronic RNA species" in Journal of General Virology, 49: 161-180 who reported that the genome of rabies virus is organized similar to that of vesicular stomatitis virus encoded by five major proteins, the nucleoprotein (N), phosphoprotein (NS) and polymerase (L) protein which, together with the genomic RNA form a nucleocapsid which is enveloped by a membrane (M) containing the transmembrane glycoprotein G. Conzehnann et al., 1990 in "Molecular cloning and complete nucleotide sequence of the attenuated rabies virus SAD B 19" Virology 175: 485-499 cloned and sequenced the complete nucleotide sequence of viral genome of SAD B 19 rabies virus strain which comprises 11, 928 nucleotides and encodes the five viral proteins N, NS M, G and L. The five cistrons are separated by intergenic regions of 2, 5, 5, and 24 nucleotides respectively.

Reference may be made to Gaudin et al, 1991 "Rabies Virus Glycoprotein is a Trimer" Virology 187, 627-632. They studied the oligomeric structure of glycoprotein both on the viral surface and after solubilization with detergents. The study shows that native quaternary structure of the glycoprotein is trimeric. However most detergents used in the study solubilized G in a monomeric form and only CHAPS a zwitterionic detergent, allowed solubilization of G in its native trimeric structure, this was determined using electron microscopy and sedimentation analysis of detergent solubilized G. The CHAPS solubilized G had a sedimentation coefficient of 9 S while other detergents solubilized G in a 4 S monomeric form. This study confirmed the results obtained by Whitt et al., 1991 "Membrane fusion activity, oligomerization and assembly of the rabies virus glycoprotein" in Virology 185, 681-688 wherein, a cross—linking reagent was used to study G expressed in HeLa cells from cloned cDNA. Electron microscopy also indicated that the native molecule has a "head" and a "stalk" and provided the basis for a low—resolution model of the glycoprotein structure.

Reference may be made to Dietzschold et al., 1983 "Characterization of an antigenic determinant of the glycoprotein that correlates with pathogenicity of rabies virus" Proc. Natl. Acad. Sci. USA; 80: 70-74 who reported that the amino acid arginine at 333 position of the glycoprotein plays a critical role in the pathogenicity of the rabies virus. Benmansour et al., 1991 "Antigenicity of rabies virus glycoprotein" Journal of Virology: 4198-4203 evaluated the relative importance of antigenic sites by describing more precisely the antigenicity of the protein by using monoclonal antibodies and neutralization—resistant (MAR) mutants. The 266 neutralizing monoclonal antibodies were identified in the study of which 97% belonged to sites II and III which were initially defined by Lafon et al., 1990 in "Human monoclonal antibodies specific for the rabies virus glycoprotein and N protein" Journal of General Virology; 71: 1689-1696.

Reference may be made from Cox et al., 1977 "Rabies virus glycoprotein 11 Biological and serological characterization" Infection Immunity 16, 743-759 wherein the glycoprotein of rabies virus was identified as a major antigen that induces protective immunity and induces the production of virus—neutralizing antibodies and confers immunity against a lethal challenge infection by the rabies virus. Although protection against rabies virus infection is probably the result of many host effector interactions, as studied by Turner 1985, "Immune response after rabies vaccination: basic aspects" Ann. Inst. Pasteur Virol. 136E: 453-460, the rabies virus G protein represents a logical choice for the development of a subunit vaccine that can be used for immunization against rabies in humans and animals. Reference in this respect can also be made from Cox et al., 1980, "Preparation and characterization of rabies hemagglutinin" Infection Immunity 30, 572-577.

Reference may be made to Swamy et al., 1984, "Neurological complication due to beta—propiolactone (BPL)—inactivated antirabies vaccination" Journal of the Neurological Sciences 63: 1: 111-128; who studied the neuroparalytic accident in patients due to antirabies vaccination with BPL vaccine which proves that the virus was not completely inactivated by beta-propiolactone and can be a high risk for the health because basically the inactivated rabies vaccines consist of suspensions of virus containing central nervous tissue of infected animals, such as rabbits or sheep or of suspensions of infected duck fetuses. Such type of vaccines also have a second drawback that, due to the high content of foreign proteins, they may cause undesired side effects at the point of injection as well as of general nature. When rabies vaccines from the central nervous tissue are used, the patient may even suffer neurocomplications with permanent damage, all the more since a series of injections is required for sufficient protection against rabies. Moreover, animal tissue based vaccines may carry other infective particles like prions and viruses like HIV, Fowl pox, Madcow etc.

Anilionis et al. 1981, "Structure of the glycoprotein gene in rabies virus" Nature: 294: 275-278 cloned the glycoprotein coding gene, using mRNA extracted from rabies virus infected BHK cells, purified by oligo (dT) cellulose chromatography and sucrose density centrifugation and determined complete nucleotide sequence of the glycoprotein cDNA. Subsequently, Yelverton et al., 1983, in "Rabies virus glycoprotein analogs: biosynthesis in *Escherichia coli*" Science: 219: 614-620 expressed the glycoprotein in *Escherichia coli*, but the protein was not immunologically active. This is because the antigenic determinants dependent on post translation modifications such as carbohydrate side—chain attachment, i.e. the introduction of the authentic carbohydrates, as it happens in eukaryotic cells is not achieved in *Escherichia coli* cells. Various other heterologous systems have been used to express the rabies glycoprotein. Two species of yeasts have been tried extensively for the expression of rabies glycoprotein. These are *Saccharomyces cerevisiae* (Kelper et al., 1993, Sakamoto et al., 1999) and *Pichia pastoris* (patent no. WO9000191, 1990). Polypeptides of 65-68 kDa, which migrated at the same molecular weight as authentic viral rabies G protein species, were synthesized by *Saccharomyces* yeast transformants as detected by immunoblotting with rabies specific antiserum. Reference may be made to Sakamoto et al., 1999, "Studies on the structures and antigenic properties of rabies virus glycoprotein analogues produced in yeast cells", Vaccine: 17: 205-218 wherein two forms of rabies virus glycoprotein produced in the G-cDNA—transfected yeast cells were identified. These were designated as YGI (66 kDa) and YGII (56 kDa). The YG1 reacted with polyclonal anti-G antibodies but did not react with conformational epitope—specific MAb. While the protein expressed in *Saccharomyces* did not protect animals challenged with rabies virus, the protein expressed in *Pichia* were claimed to provide protection (WO 90000191 dated 1990). However, the details have not been published, nor has the *Pichia* system been used and may therefore not be a system of choice. The same G-cDNA was expressed in animal cells, a single form was produced. The results concluded that most G protein molecules were not processed normally in yeast cells. The crucial role of rabies glycoprotein in protection was determined by Foley et al., 2000 "A recombinant rabies virus expressing vesicular stomatitis virus glycoprotein fails to protect against rabies virus infection" in Proc. Natl. Acad. Sci.: 97; 26: 14680-14685, constructed a recombinant RV (rRV) in which rabies virus glycoprotein ectodomain and transmembrane domains were replaced with the corresponding regions of vesicular stomatitis virus (VSV) glycoprotein and immune response was studied and compared to parental rRV strain containing rabies virus glycoprotein. Similar immune responses against the internal viral proteins of both viruses indicated successful infection but all mice who received the rRV vaccine survived the challenge, whereas immunization with the domain substituted rRV-VSV-G did not induce protection. Which confirmed the critical and crucial role of glycoprotein of rabies virus and also demonstrated that immune response and immunoprotection against challenge with live rabies virus are two different phenomenon.

Expression of rabies glycoprotein gene by baculoviral vectors in insect cells gives high yields of protein to the extent of 18% of total cellular protein, 48 h post infection. In one study (Prehaud D H et al, 1989) the gene encoding the G protein of CVS strain was placed under the control of the AcNPV polyhedrin promoter and expressed at high levels by the derived recombinant virus using a *Spodoptera fugiperda* cell-line. The insect derived protein exhibited slightly faster electrophoretic mobility due to differences in the glycan components. Vaccination by insect derived glycoprotein, followed by challenged to mice gave delayed mortality, i.e., a low level of protection against rabies.

In another study, Rupprecht et al (1993) demonstrated that a glycoprotein (ERA strain) derived from recombinant baculovirus—infected insect cells was efficacious as an oral vaccine in raccoons. In view of relatively high costs of the insect and mammalian cell-systems these are not the systems of choice for G protein expression as a strategy to develop vaccine against rabies.

Some of the recombinant Pox virus rabies glycoprotein based vaccines licensed and marketed in US since 2000 are (i) Purevax for Feline rabies (cats)—monovalent, live canary pox vector (Merial Inc.) and (ii) Raboral V-RG for raccoons-oral live vaccinia vector. Recombinant Poxviruses (USPTO 5266313 dated 1986; USPTO 05348741 dated 1994) have many useful features as vectors for the expression of genes that carry immunizing antigens from other viruses. These are easy to produce and induce cellular and humoral immunity. However, there is concern about the safety of vaccinia virus, if used widely for men and animals.

A Canarypox virus Alvac-RG (vCP65) was used as a vector in non-avian species (Taylor et al., 1995) for expressing the rabies glycoprotein G gene (USPTO 5843456 dated 1998) to address the concern about the spread of vaccinia virus to non-target population, especially immunocompromised individuals. Avipox virus was also developed as a vector for expressing rabies glycoprotein gene. Avipoxvirus (canarypox) recombinants (USPTO 6340462 dated 2002) undergo abortive replication in nonavian cells, yet can achieve expression of extrinsic gene products and their presentation to the immune system. In vitro studies have shown that no replication of the virus can be detected on six human-derived cell lines, nor can the virus be readily adapted to replicate on non-avian cells. Expression of the rabies G was detected on all cell lines analyzed in the absence of productive viral replication. The safety and efficacy of the recombinant (Alvac-RG; vCP65) were tested in several animal species, then it was subjected to a phase 1 clinical trial. This study showed the potential of non-replicating poxviruses as vectors for vaccination in human beings (Fries et al., 1996). Recombinant were immunogenic by the intramuscular and subcutaneous routes. They were also immunogenic when given orally.

The viral vectors including posvirus vectors provide a convenient vehicle for the delivery of the vaccines. This also reduces the costs involved in purifying the proteins from cultures. However, owing to safety considerations, viral vectors meant for humans go through tougher scrutiny for approval by the regulatory bodies.

Cell-cultured based vaccines for rabies are limited to growing inactivated strains of the virus in cell cultures. These include, the relatively expensive Human Diploid Cell Vaccines (HDCV), purified Vero Cell Rabies vaccine (Verorab) and the more economical primary chick embryo cell culture vaccine (PCEV-Rabipur). These vaccines comprise the virus grown in cell cultures. Current biotechnological approaches aim at expressing the coat protein gene of the rabies virus to develop a safe RGP that could be deployed as an active vaccine.

The expression of proteins or safe 'subunit vaccines' in cell-cultures is a routine procedure in recent years. Examples of such useful host cell-lines are VERO and HeLa cells, Chinese Hamster Qvary (CHO) cell lines, and W 138, Baby Hamster Kidney (BHK), COS-7 and MDCK cell-lines. Stable expression of rabies virus glycoprotein was shown in Chinese Hamster Ovary cells (Burger et al., 1991). A full length, glycosylated protein of 67 K that co-migrated with the G-protein isolated from virus-infected cells, was obtained.

The rabies glycoprotein expressed in different cell-lines was similar to the native protein in terms of size and immunoreactivity. The recombinant protein thus produced provided an insight into the biology of the protein and gave a clue to the parameters to be taken into consideration while choosing an appropriate expression system. The proteins were of analytical grade and can be purified to a high degree of purity. However, the process based on animal cell lines is very expensive for industrial scale. In order to decide upon an economically viable alternative, the expression system should combine in itself the options for fermentor level scaling up (as in bacteria) and the option for producing a fully glycosylated protein that is closely similar to the native form (as in cell-lines). Expression in plants is a promising alternative in this respect.

Subunit vaccines are important improvements over conventional attenuated or killed vaccines in many aspects including safety and production systems. The expression of foreign proteins in plants has become an attractive alternative in recent years as it has the potential of producing recombinant proteins in large quantities and at low cost. Recent advances in genetic engineering have provided the requisite tools to transform plants to express foreign gene. *Agrobacterium tumefaciens* have proven to be efficient and highly versatile vehicles for the expression of industrially valuable foreign genes into the plant tissue, as described in Hood et al. (1999) "Plant—based production of xenogenic proteins" Current Opinion in Biotechnology 10: 382-386. Vaccine for human and animal disease prevention comprise the most competitive area for plant based production of xenogenic proteins. Utilization of plants as expression vectors for the production of foreign proteins has captured attention in recent years. Viral proteins (HbsAg, Norwalk virus capsid protein, rabies virus glycoprotein, FMDV structural protein VP1), bacterial toxins (LTB), antibody molecules and several other industrially and therapeutically important proteins have been expressed successfully in plants (Tacket et al., 2000; Kong et al., 2001). In most cases the expressed proteins are fully functional as antigens or in ligand recognition. Importantly, they are effective in eliciting in eliciting specific immune responses. The production of immunogens in plants might be an economic alternative to animal cell based production systems for the development of vaccine. The greatest advantage of using plant systems for the expression of therapeutically important proteins is the absence of human or animal pathogens like HIV, Fowl Fox, Mad Calf, prions etc. in the protein preparations made from plants. Yet another possibility is of utilizing the plant material directly as a feed, thus generating an edible vaccine. Although there is a lot of scope for studies on high—level protein accumulation, post—translational protein modifications and downstream processing, enough progress has been made to arouse interest in plants as robust and commercially viable systems.

The simplistic requirements of plants for sunlight, water and minerals makes them an inexpensive means of correctly processing and expressing proteins that can be quite complex. The traditional subunit vaccines are expensive to produce and not heat stable necessitating a 'cold-chain' en rote from manufacturer to vaccination. This limits their availability and use in low-funded health care systems of developing countries. However, proteins expressed in plant parts are often stable for years, as for example, the seed proteins.

A bacterial antigen (*E. coli* enterotoxin) produced in transgenic plants was shown to effectively immunize mice when the crude protein extracts from the transgenic plant tissue were administered orally, as shown by Curtiss and Cardineau, 1997 in "Oral immunization by transgenic plants" U.S. Pat. No. 5,686,079 and Haq et al., 1995 in "Oral immunization with a recombinant bacterial antigen produced in plants" Science 268: 714-716. The work of Haq and co-workers was followed by human clinical trials to show that humans do develop an immune response to antigen delivered in uncooked food as referred by Tackett et al., 1998 "Immunogenicity in humans of a recombinant bacterial antigen delivered in transgenic potato". Nature Medicine 4: 607-609.

Reference may be made to McGarvey et al., 1995 "Expression of the rabies virus glycoprotein in transgenic tomatoes" Bio/technology 13: 1484-1487 who engineered tomato plants (*Lycopersicon esculentum*) to express a gene for the rabies glycoprotein (G-protein) under the control of the 35S' promoter of cauliflower mosaic virus. The protein was expressed in tomato and showed molecular weight of 62 and 60 kDa in western blot after immunoprecipitation, as compared to 66 kDa observed for G protein from virus grown in BHK cells. The amount of G protein immunoprecipitated was found to be approximately 1-10 ng/mg of soluble protein i.e. at 0.0001% to 0.001% of soluble protein. The low expression level may have been due to using a poorly designed gene. For example, a native G protein coding gene was used along with its native signal peptide The inventors did not examine antigenicity of the G protein and therefore it is not possible to comment on biological activity and utility of the G protein expressed in tomato plant or the gene designed in that study, specially for therapeutic purpose.

Plant derived immune response against diseases such as mink enteritis and rabies were reported by expressing viral epitopes on the surface of plant viruses, followed by infection of susceptible host with the recombinant modified virus, reference can be made from Modelska et al., 1998 "Immunization against rabies with plant—derived antigen" Proc. Natl. Acad. Sci. USA 95: 2481-2485 and Yusibov et al., 2002, "Expression in plants and immunogenicity of plant virus—based experimental rabies vaccine". The plant virus was purified from the tissue and administered to the test animals. Although this system is very effective, the size of the antigen polypeptide that can be expressed on surface of a vector virus is limited to 37 amino acids. Hence epitope mapping of the antigen is needed for this approach. Such thorough knowledge of the antigen is not generally available, especially with newly discovered diseases where the expression of full-length proteins may be the only option. Also several epitopes need to be identified and joined together since a single epitope may not give acceptable protection against challenge by the pathogenic virus. Furthermore, containment could be considered as a significant problem at the agricultural level, especially when environmentally stable viruses like TMV are used.

SUMMARY OF THE INVENTION

One object of the present invention is to provide a recombinant chimeric G-protein based rabies vaccine having SEQ ID No 1 and its parts or variants thereof.

Another object of the present invention is to provide a chimeric gene of SEQ ID No. 2, encoding chimeric G-protein based rabies vaccine having SEQ ID No 1.

Still another object of the present invention is to provide a method for generating large scale chimeric G-protein based rabies vaccine.

Yet another object of the present invention is to provide a method of vaccinating a subject for rabies.

In some embodiments of the present invention, the G-protein based rabies vaccine comprises 1-26 amino acid residues of PR-S signal peptide at N-terminal, followed by 27-32 six hexahistidine tag residues (SEQ ID NO: 55), 33-36 amino acid residues of tetrapeptide of factor Xa proteolytic cleavage site, 37-541 amino acid residues of mature glycoprotein G of ERA strain of rabies virus, 542-547 amino acid residues of six amino acid long for retention of the chimeric G protein in endoplasmic reticulum at C-terminus extreme of the chimeric protein.

BRIEF DESCRIPTION OF FIGURES

FIG. 1 provides a comparison of the nucleotide sequence of the chimeric G protein gene (SEQ ID NO: 2) of the present invention to the native G protein gene (SEQ ID NO: 63).

FIG. 2 provides a comparison of the amino-acid sequences of the chimeric G protein (SEQ ID NO: 1) and native G protein (SEQ ID NO: 64).

FIG. 3 depicts a novel chimeric G protein gene in a cloning vector. (His)$_6$ and SEKDEL disclosed as SEQ ID NOS 55 and 59, respectively.

FIG. 6 shows the anti-rabies immuneresponse in Balb/c mice injected interperitioncally with rabies virus glycoprotein. Antibody titres after second and third boosters, are shown. PIS (pre-immunization serum), CON (control mice, injected with phosphate buffer), PDP (mice injected with the plant derived glycoprotein fraction of tobacco leaves), V (mice injected with commercial Rabipur vaccine). In each case, five mice were injected.

FIG. 7 shows the immunoprotection of Balb/c mice after intracerebral challenge with live rabies virus. The five mice whose immuneresponse is shown in FIG. 7 were challenged with live CVS virus maintained at Indian Veterinary Research Institute, Izatnagar, India. Per cent survival in mice vaccinated with phosphate buffer, plant derived rabies virus glycoprotein and commercial Rabipur vaccine are shown.

DETAILED DESCRIPTION OF INVENTION

Figure 4:
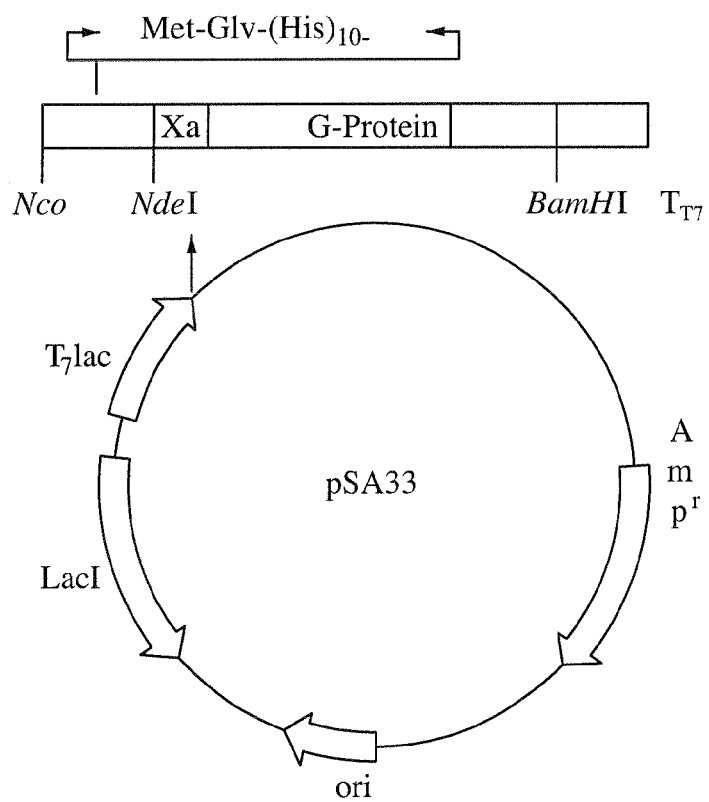
FIG. 4 depicts the *E. coli* expression cassette used for expressing the chimeric protein in *E. coli*. Peptide disclosed as SEQ ID NO: 65.

Accordingly the present invention provides a recombinant chimeric G-protein having SEQ ID No. 1 and its parts or variants thereof.

In an embodiment of the present invention, the length of the chimeric G-protein comprises 547 amino acids or its parts and variants thereof.

In a further embodiment of the present invention, the chimeric G-protein comprises amino acid residues of PR-S signal peptide at N-terminal at position 1 to 26, followed by six hexahistidine tag (SEQ ID NO: 55) residues at 27-32 position, amino acid residues of tetrapeptide of factor Xa proteolytic cleavage site at 33-36 position, amino acid residues of mature glycoprotein G or ERA strain of rabies virus at 37 to 541 position and, six amino acid long residue at C-terminus extreme of the chimeric protein at position 542 to 547 for retention of the chimeric G protein in endoplasmic reticulum.

In another embodiment, the present invention provides a recombinant chimeric G-protein based rabies vaccine having SEQ ID No. 1 and its parts or variants thereof expressed in plant tissue. In a further embodiment, the chimeric G-protein is of length 547 amino acids in the vaccine. In yet a further embodiment, the chimeric G-protein comprises 1-26 amino acid residues of PR-S signal peptide at N-terminal, followed by 27-32 six hexahistidine tag (SEQ ID NO: 55) residues, 33-36 amino acid residues of tetrapeptide of factor Xa proteolytic cleavage site, 37-541 amino acid residues of mature glycoprotein G of ERA strain of rabies virus, 542-547 amino acid residues of six amino acid long for retention of the chimeric G protein in endoplasmic reticulum at C-terminus extreme of the chimeric protein.

In yet another embodiment of the present invention, the recombinant chimeric G-protein gene encodes a protein having immunoprotective activity against live rabies virus.

In still another embodiment of the present invention, the vaccine provides 100% immunoprotection against rabies virus.

In still another embodiment of the present invention, the vaccine controls rabies in humans, pets and wild life.

Further, the present invention also provides a chimeric gene of SEQ ID No. 2, encoding chimeric G-protein based rabies vaccine.

In an embodiment of the present invention, the chimeric gene of SEQ ID No. 2 comprises 1.67 kb.

Present invention also provides a set of 52 primers of SEQ ID No. 3 to 54 is useful for the synthesis of chimeric gene of SEQ ID 2.

In an embodiment of the present invention, all oligonucleotides are synthesized chemically and fused enzymatically to obtain desired double stranded DNA.

Further, the present invention also provides an economical method for generating large scale chimeric G-protein based rabies vaccine by expressing novel chimeric gene SEQ ID No. 2, for control rabies, wherein the said process comprising the steps of:

a) designing and constructing a gene consisting of recombinant chimeric G-protein comprising of 1-26 amino acid residues of PR-S signal peptide at N-terminal, followed by 27-32 six hexahistidine tag (SEQ ID NO: 55) residues, 33-36 amino acid residues of tetrapeptide of factor Xa proteolytic cleavage site, 37-541 amino acid residues of mature glycoprotein G of ERA strain of rabies virus, 542-547 amino acid residues of six amino acid long for retention of the chimeric G protein in endoplasmic reticulum at C-terminus extreme of the chimeric protein having SEQ ID No. 1;

b) designing a 1.67 kb chimeric gene of SEQ ID No.2 to code for the chimeric G-protein given in step (a);

c) introducing 34 unique restriction sites and creating HindIII and XbaI restriction sites upstream and BamHI and SacI downstream of the gene obtained in step (b);

d) cloning the gene of step (c) in plasmid pBluescriptII SK(+) (pSA17);

e) excising the HindIII-SacI fragment of recombinant G-protein from pSA17;

f) ligating the fragment obtained in step (e) with Ti binary vector pBI101 at HindIII-SacI site to form plasmid vector pSA5, wherein Ti binary vector pBI101 comprises of CaMV35S promoter with duplicate enhancer and Nos transcription terminator;

g) transforming the plasmid vector pSA5 obtained in step (f) to *A.tumenifaciens* strain LBA4404 (pAL4404);

h) transforming strain of *A.tumenifaciens* obtained in step (g) to *Nicotiana tabacum* (Tobacco) plants;

i) obtaining transgenic plants of tobacco expressing the recombinant chimeric G-protein gene; and j) confirming the presence of recombinant chimeric G-protein gene in transgenic plants obtained from step (i) by molecular characterization.

In an embodiment of the present invention, the strain of rabies virus is selected from the group consisting of ERA strain, CVS strain etc.

In another embodiment of the present invention, the PR-S signal peptide is replaced with another comparable signal peptide, e.g., PR-1 or any other signal peptide, depending on the plant expression system for transport of the protein to endoplasmic reticulum.

In yet another embodiment of the present invention, the protein is of length 547 amino acids.

In still another embodiment of the present invention, the hexa histidine residue can be replaced with any other peptide selected from the group consisting of cellulose binding domain, streptavidin agarose binding domain, glutathione-S-transferase fusion etc. having affinity to a matrix for purification.

In still another embodiment of the present invention, four amino acid residues for cleavage can be replaced with any endo-protease selected from the group consisting of bovine enterokinase, thrombin, factor Xa etc.

In still another embodiment of the present invention, a polypeptide of four amino acid residues is introduced at the downstream of histidine residue to allow enzymatic cleavage of the histidine residues after purification of chimeric G-protein on metal chelate affinity column.

In still another embodiment of the present invention, other amino acid residues of similar applications, such as Asp Asp Asp Asp Lys ↓ (SEQ ID NO: 56), Leu Val Pro Arg ↓ Gly Ser (SEQ ID NO: 57), Ile Glu Glu Arg ↓ (SEQ ID NO: 58), may be used to replace cleavage site amino acid residues of protein vaccine of SEQ ID No.1.

In still another embodiment of the present invention, a hexapeptide may be introduced at the C-terminus extreme of the chimeric protein for its retention in lumen of endoplasmic reticulum. In further embodiments, other retention signal may be equally good for targeting and accumulation of the chimeric G-protein in vacuole, golgibody, microtubules and microsomes or any other organelle.

In still another embodiment of the present invention, recombinant chimeric G-protein gene encodes a protein having immunoprotective activity against live rabies virus.

In still another embodiment of the invention, the vaccine controls rabies in humans, pets and wild life.

In still another embodiment of the present invention, plants for expressing recombinant G-protein gene is selected from group consisting of tobacco, corn, legumes like chickpea, pigeonpea, groundnut, soybean, vegetables like tomato, potato, musk melon, water melon, spinach, cauliflower, cabbage, chili, *capsicum*, carrot, and/or other plants and lower plant selected from any algae.

In still another embodiment of the present invention, the novel chimeric G protein may be partially purified from total soluble protein from the leaf of the transgenic tobacco plants.

In still another embodiment of the present invention, the protein is 2-4 fold more immunogenic as compared to inactivated virus. For example, as shown in example 2 in table 3 and FIG. 6.

In still another embodiment of the present invention, the vaccine expression is about 0.2% of total soluble protein in plant.

In yet another embodiment, the present invention also provides a method of vaccinating a subject for rabies, wherein the said method comprising administering of pharmaceutical effective amount of recombinant chimeric G-protein gene vaccine. In a further embodiment the vaccine is produced and expressed in transgenic plants, optionally along with pharmaceutical acceptable additive(s) to the subject.

In an embodiment of the present invention, the subject is human, pets and wild life. In yet another embodiment of the present invention, the administration of the plant expressed vaccine is through routes commonly known in the art, including, but not limited to, oral, intrapertional etc.

In still another embodiment of the present invention, the recombinant chimeric G-protein gene vaccine is administered at concentration ranging from ng to µg quantities, depending upon purity of the protein. In a preferred embodiment µg amounts may be administered. See examples 2 and 3.

In still another embodiment of the present invention, the vaccine is safe for the administration.

In still another embodiment of the present invention, the vaccine is expected to be stable for a long time, when expressed in different plant parts and tissues, specially seeds, tubers, roots, leaves etc. For example, proteins stored in seeds are known to be stable for several years.

In still another embodiment of the present invention, the antibody titre of the protein is in the range of 0.365±0.20 after IInd booster dose and 0.833±0.20 after IIrd booster dose. See example 2.

In still another embodiment of the present invention, the said vaccine provides 100% immunoprotection.

Present invention relates to a chimeric G-protein of ERA strain of rabies virus and a synthetic gene to encode a strategically designed recombinant protein. Chimeric G-protein, 547 amino acid residues long. The chimeric G-protein may be strategically designed by replacing the native signal polypeptide (from position 1 to 19) of ERA strains of rabies (EMBL: RHRBGP) by that of PR-S of tobacco (from position 1 to 26). ERA (Evelyn Rokitniki Abelseth) is a well known rabies vaccine strain which is a derivative of wild type rabies virus strain SAD (Street Albama Duffering). SAD strain belongs to serotype I under which most of the classical rabies virus strains are grouped. It has been determined that ERA strain of rabies functions as the most efficient vaccine at mouse intracerebral lethal dose 50% ($MCLD_{50}$). It produces the titer to the magnitude of $10^5$-$10^7$ $MICLD_{50}$/0.03 ml in various tissue culture cell line. Hence the G protein gene of ERA strain was selected for the study. Hence, to develop a plant based vaccine. ERA is one of the well studies strains of rabies virus. Genes corresponding to other strains like CVS etc. will also be appropriate for developing plant based vaccine technology.

A total of six histidine residues (SEQ ID NO: 55) and a tetrapeptide representing the cleavage site of factor Xa were designed between signal peptide and mature G-protein. A hexapeptide for anchoring the chimeric protein in endoplasmic reticulum was included at the C-terminus of the chimeric protein. In this way, chimeric G-protein comprises amino acid residues 1-26 of PR-S signal peptide of tobacco, 27-32 of six histidine residues (SEQ ID NO: 55), 33-36 of cleavage site for factor Xa, 37-541 of mature G-protein of ERA strain of rabies virus and 542-547, a hexapeptide for localization in endoplasmic reticulum.

TABLE 1

Parameters followed for designing the rabies glycoprotein coding gene for high level expression in plants (SEKDEL peptide disclosed as SEQ ID NO: 59).

| | Rabies glycoprotein gene | |
|---|---|---|
| Parameter | Native | Designed |
| GC content | 47.5% | 53.6% |
| TA ending codons | 30 | 4 |
| CG ending codons | 11 | 3 |
| Hair pin loops with ΔG below -4.0 kcal/mole | 22 | 0 |
| Putative polyadenylation & RNA instability sequences (splice sites, A/T strings) | 12 | 0 |
| Translational initiation context | Unknown | TAAACA<u>ATG</u> |
| Additional 3' codons | Not applicable | 18 nucleotides coding for SEKDEL |
| 5' signal peptide | Native 19 residue | 26 residue tobacco PRs |

A 1.67 kb nucleotide sequence was theoretically designed to code for the above-mentioned chimeric G-protein. The gene encoding such a chimeric protein, was designed for high-level expression in plants. The plant preferred codons for each amino acid were distributed evenly to facilitate efficient translation. A translation initiation context appropriate to achieve high level of gene expression in plants (TAAA-CAATGAAC (SEQ ID NO: 60)) was included at 5' extreme and two translation stop codons were introduced at the end of the reading frame of the chimeric protein. A total of 34 unique restriction sites were introduced uniformly throughout the length of the gene at intervals of 40-80 bp. The HindIII and XbaI restriction sites were created at the upstream and BamHI and SacI at the downstream of the gene to facilitate its cloning. The gene was divided into 50 overlapping oligonucleotides (48 to 50 nucleotides long) with 10 to 16 base long gaps in between. Each oligonucleotide had 13-18 nucleotide long overlap with the immediately adjacent oligonucleotides on the complementary strand. The complementary overlaps were designed to keep $T_m$ value between 48-50° C. The oligonucleotides were synthesized on a DNA synthesizer (Gene Assembler Special, Pharmacia, Sweden) at 200 nmole scale and purified on denaturing urea-PAGE. All 50 oligonucleotides were assembled into 1.67 kb double-stranded DNA, herein said chimeric G-protein gene following the ligation-free gene synthesis method of Singh et al. (1996) and as shown in FIG. 3. The DNA was digested with HindIII and SacI restriction enzymes and cloned in pBluescriptII SK(+) (Stratagene, La Jolla, Calif.). The plasmid was named as pSA17 (FIG. 3). The nucleotide sequence of the synthetic DNA was confirmed by sequencing the cloned synthetic DNA on automated DNA sequencing system (Applied Biosystems model 377A).

A cassette was constructed also for the expression of the modified gene in *E. coli* under the control of T7lac promoter. A suitable set of primers was separately designed to amplify the DNA coding for the mature G-protein (1545 bp) and create NdeI and BamHI restriction sites. The plasmid pSA17 was amplified; DNA was digested with the restriction enzymes NdeI and BamHI and cloned in expression vector pET-19b (Novagen, Madison Wis.). The plasmid was named as pSA33 (FIG. 4). *E. coli* BL21DE3 strain was transformed with the construct pSA33. The recombinant protein was expressed by induction with appropriate concentrations of IPTG (1 mM). The expression was carried out at 37° C. for different time period. *E. coli* cells were lysed with SDS PAGE loading buffer and resolved on 10% denaturing polyacrylamide gel. The *E. coli* DE3 BL21 (pSA33) expressed the recombinant protein of expected molecular size i.e., 60.65 kDa which is comparable to that of protein molecular weight determined by protein molecular analysis programme using a website http://www.cbio.psu.edu of modified gene. This confirmed that synthetic gene for the G-protein was developed correctly.

As used here, reference to the "chimeric G-protein" means, the chimeric fusion of PR-S signal peptide, histidine tag, cleavage site for factor Xa, mature G-protein tagged with endoplasmic reticulum retention signal, which shows a high immunoprotection activity in mice against live virus challenge.

A person skilled in this art can use any other suitable plant, animal, virus, insect, microbial signal peptide to express the chimeric G-protein. Such protein can be expressed in respective system. The histidine tag and the cleavage site for factor Xa are essentially included to facilitate purification of the chimeric G protein from plant leaf extract. These are not essential to immunoprotection and can be substituted by other alternative strategies to facilitate protein purification. After purification, such molecule can be used as subunit vaccine for the management of rabies in pets, wild life and humans. Such subunit vaccine can be given as such or in combination DNA vaccine and/or inactivated virus. Such chimeric protein can also be used as oral vaccine.

The gene and chimeric G-protein are useful according to the subject invention and include not only 547 amino acid long protein expressed in plants but also parts of the sequence, variants and mutants, which retain the high immunoprotective activity of the mature G-protein specifically exemplified herein. As used here, the terms "variants" or "variations" of genes refer to nucleotide sequences, which encode the same chimeric protein or which encode chimeric protein having lower or equivalent biological activity in terms of immune response and immunoprotection in mice and other animals. In minor variant, addition, deletion or acceptable substitution of a few amino acids may give an equally effective rabies vaccine. As used here, the term "equivalent biological activity" refers to chimeric protein having similar or essentially the same immunological and immunoprotective activity with applications in diagnostics, therapeutics and prophylaxis.

With reference to SEQ ID No 1, several of its variants are expected to be functionally active because they may lead to change from one amino acid to another closely related amino acid. Such a substitution often does not lead to any effect on activity of the protein. Similarly, deletion or addition of a few amino acids may not lead to a significant effect on function of the protein. Examples of amino acid substitutions that may not often effect function of a protein are given in

TABLE 2

Such substitutions will have little or no effect specially when these are at positions in amino acid sequence that do not participate in 'functional' or 'active site' of the protein.

| | C | G | P | S | A | T | D | E | N | Q | H | K | R | V | N | I | L | F | Y | W |
|---|---|---|---|---|---|---|---|---|---|---|---|---|---|---|---|---|---|---|---|---|
| C | 12 | −3 | −3 | 0 | −2 | −2 | −5 | −5 | −4 | −5 | −3 | −5 | −4 | −2 | −5 | −2 | −6 | −4 | 0 | −1 |
| G | −3 | 5 | −1 | 1 | 1 | 0 | 1 | 0 | 0 | −1 | −2 | −2 | −3 | −1 | −3 | −3 | −4 | −5 | −5 | −7 |
| P | −3 | −1 | 6 | 1 | 1 | 0 | −1 | −1 | −1 | 0 | 0 | −1 | 0 | −1 | −2 | −2 | −3 | −5 | −5 | −6 |
| S | 0 | 1 | 1 | 1 | 1 | 1 | 0 | 0 | 1 | −1 | −1 | 0 | 0 | −1 | −2 | −1 | −3 | −3 | −3 | −2 |
| A | −2 | 1 | 1 | 1 | 2 | 1 | 0 | 0 | 0 | 0 | −1 | −1 | −2 | 0 | −1 | −1 | −2 | −4 | −3 | −6 |
| T | −2 | 0 | 0 | 1 | 1 | 3 | 0 | 0 | 0 | −1 | −1 | 0 | −1 | 0 | −1 | 0 | −2 | −3 | −3 | −5 |
| D | −5 | 1 | −1 | 0 | 0 | 0 | 4 | 3 | 2 | 2 | 1 | 0 | −1 | −2 | −3 | −2 | −4 | −6 | −4 | −7 |
| E | −5 | 0 | −1 | 0 | 0 | 0 | 3 | 4 | 1 | 2 | 1 | 0 | −1 | −2 | −2 | −2 | −3 | −5 | −4 | −7 |
| N | −4 | 0 | −1 | 1 | 0 | 0 | 2 | 1 | 2 | 1 | 2 | 1 | 0 | −2 | 0 | −2 | −3 | −4 | −2 | −4 |
| Q | −5 | −1 | 0 | −1 | 0 | −1 | 2 | 2 | 1 | 4 | 3 | 1 | 1 | −2 | −1 | −2 | −2 | −5 | −4 | −5 |
| H | −3 | −2 | 0 | −1 | −1 | −1 | 1 | 1 | 2 | 3 | 6 | 0 | 2 | −2 | −2 | −2 | −2 | −2 | 0 | −3 |
| K | −5 | −2 | −1 | 0 | −1 | 0 | 0 | 0 | 1 | 1 | 0 | 5 | 3 | −2 | 0 | −2 | −3 | −5 | −4 | −3 |
| R | −4 | −3 | 0 | 0 | −2 | −1 | −1 | −1 | 0 | 1 | 2 | 3 | 6 | −2 | 0 | −2 | −3 | −4 | −5 | 2 |
| V | −2 | −1 | −1 | −1 | 0 | 0 | −2 | −2 | −2 | −2 | −2 | −2 | −2 | 4 | 2 | 4 | 2 | −1 | −2 | −6 |
| N | −5 | −3 | −2 | −2 | −1 | −1 | −3 | −2 | 0 | −1 | −2 | 0 | 0 | 2 | 6 | 2 | 4 | 0 | −2 | −4 |
| I | −2 | −3 | −2 | −1 | −1 | 0 | −2 | −2 | −2 | −2 | −2 | −2 | −2 | 4 | 2 | 5 | 2 | 1 | −1 | −5 |
| L | −6 | −4 | −3 | −3 | −2 | −2 | −4 | −3 | −3 | −2 | −2 | −3 | −3 | 2 | 4 | 2 | 6 | 2 | −1 | −2 |
| F | −4 | −5 | −5 | −3 | −4 | −3 | −6 | −5 | −4 | −5 | −2 | −5 | −4 | −1 | 0 | 1 | 2 | 9 | 7 | 0 |
| Y | 0 | −5 | −5 | −3 | −3 | −3 | −4 | −4 | −2 | −4 | −0 | −4 | −5 | −2 | −2 | −1 | −1 | 7 | 10 | 0 |

TABLE 2-continued

Such substitutions will have little or no effect specially when these are at positions in amino acid sequence that do not participate in 'functional' or 'active site' of the protein.

| W | −1 | −7 | −6 | −2 | −6 | −5 | −7 | −7 | −4 | −5 | −3 | −3 | −2 | −6 | −4 | −5 | −2 | 0 | 0 | 17 |
|---|----|----|----|----|----|----|----|----|----|----|----|----|----|----|----|----|----|---|---|----|
|   | C  | G  | P  | S  | A  | T  | D  | E  | N  | Q  | H  | K  | R  | V  | N  | I  | L  | F | Y | W  |

Table No. 2. Matrix presenting the acceptability of amino acid substitution in proteins. Single letter codes are given for amino acids along rows and columns.

A positive numeral in the matrix indicates that a given substitution may be acceptable. A negative numeral indicates non acceptability. For example, Cysteine (C) can be substituted by self (score=12) only but not by any other amino acid (all scores being negative, e.g. the score for cysteine to glycine G is −3 and therefore, not acceptable. On the other hand, glycine (G) can be substituted by self (score 5) but also by serine—S (score 1), alanine—A (score 1) and aspartic acid—D (score 1). the extent of positivity suggests the confidence level in the substitution being successful (Dayhoff, M. O., Schwartz, R. M., Orcutt, B. C. 1978. "A model of evolutionary change in proteins." In "Atlas of Protein Sequence and Structure" 5(3) M. O. Dayhoff (ed.), 345-352. National Biomedical Research Foundation, Washington.

With reference to SEQ ID No2 and the corresponding primers in SEQ ID No 3 to 54, several variants of the DNA sequence will not cause a change in function of the nucleic acid. For example, Table 3 gives a list of codons that code for the same amino acid. Such codons can be substituted for one another in a gene, without any effect on the protein sequence coded by the gene.

TABLE No. 3

Acceptable substitutions in codons in DNA sequence

| Amino acid | Single letter code for amino acid | DNA codons that can substitute for one another |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Stop codons | Stop | TAA, TAG, TGA |

It is well within the skill of a person trained in the art to create alternative DNA sequences encoding the same or essentially the same, protein. These variant DNA sequences are within the scope of the subject invention. As used herein, reference to "essentially the same" sequence refers to sequences, which have amino acid substitutions, deletions, additions or insertions, which do not materially affect immunoprotective activity. Fragments retaining immunoprotective activity are also included in this definition.

A novel chimeric G-protein of the subject invention has been specifically exemplified herein. It should be readily apparent that the subject invention comprises variants or equivalent protein (and nucleotide sequences encoding equivalent protein) having the same or similar immunoprotective activity of the exemplified chimeric protein expressed in plant or plant cells. Equivalent protein will have amino acid homology with the exemplified protein. This amino acid homology will typically be greater than 75%, preferably be greater than 90% and most preferably be greater than 95%. The amino acid homology will be highest in critical regions (antigenic epitopes) of the chimeric protein, which account for the immunoprotective activity or are involved in the determination of three-dimensional configuration, which ultimately is responsible for the biological activity. In this regard, certain amino acid substitutions are acceptable and can be expected if these substitutions are in regions, which are not critical in biological activity or are conservative amino acid substitutions, which do not affect the three-dimensional configuration of the molecule. For example, amino acids may be placed in the following classes: non-polar, uncharged polar, basic and acidic. Conservative substitutions whereby an amino acid of one class is replaced with another amino acid of the same class fall within the scope of the subject invention so long as the substitution does not materially alter the biological activity of the rabies G protein. Table 4 provides a listing of examples of amino acids belonging to such classes.

TABLE 4

| Class of Amino Acid | Examples of Amino Acids |
|---|---|
| Non-polar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the chimeric protein. It is well within the skill of a person trained in the art of protein engineering to substitute at many places, the amino acids of the chimeric G-protein with alanine since that does not often change conformation of proteins. Such substitutions are also well within the scope of the invention.

A gene encoding the chimeric G-protein of the subject invention can be introduced into a wide variety of plant virus vectors. Expression of the chimeric gene results in intracellular production and maintenance of the immunoprotective protein. Such virus can be used as a system for production and purification of chimeric G-protein. Suitable viral hosts are Badnavirus, Caulimovirus, SbCMV-like virus, CsVMV-like viruses, RTBV-like viruses Petunia vein clearing-like viruses, Mastrevirus, Curtovirus, Begomovirus, Alfamovirus or Ilarivirus (Koprowski et al., 2000:U.S. Pat. No. 6,042,832 and 2002: U.S. Pat. No. 6,448,070) Cumovirus Closterovirus, Cmivirus, Comovirus, Fabavirus, Nepovirus, Potyvirus, Rymovirus, Bymovirus, Sequivirus, Waikavirus, Carmovirus, Dianthovirus, Machlomovirus, Necrovirus, Tombusvirus, Capillovirus, Carlavirus, Enamovirus, Furovirus, Hordeivirus, Idaeovirus, Luteovirus, Marafivirus, Potexvirus, Sobemovirus, Tenuivirus, Tobamovirus, Tobravirus, Trichovirus, Tymovirus, Umbravirus, Cytorhabdovirus, Nucleorhabdovirus, Tospovirus, Alphacryptovirus, Betacryptovirus, Fijivirus, Phytoreovirus, Oryzavirs to developed production system for chimeric G protein.

Figure 5:
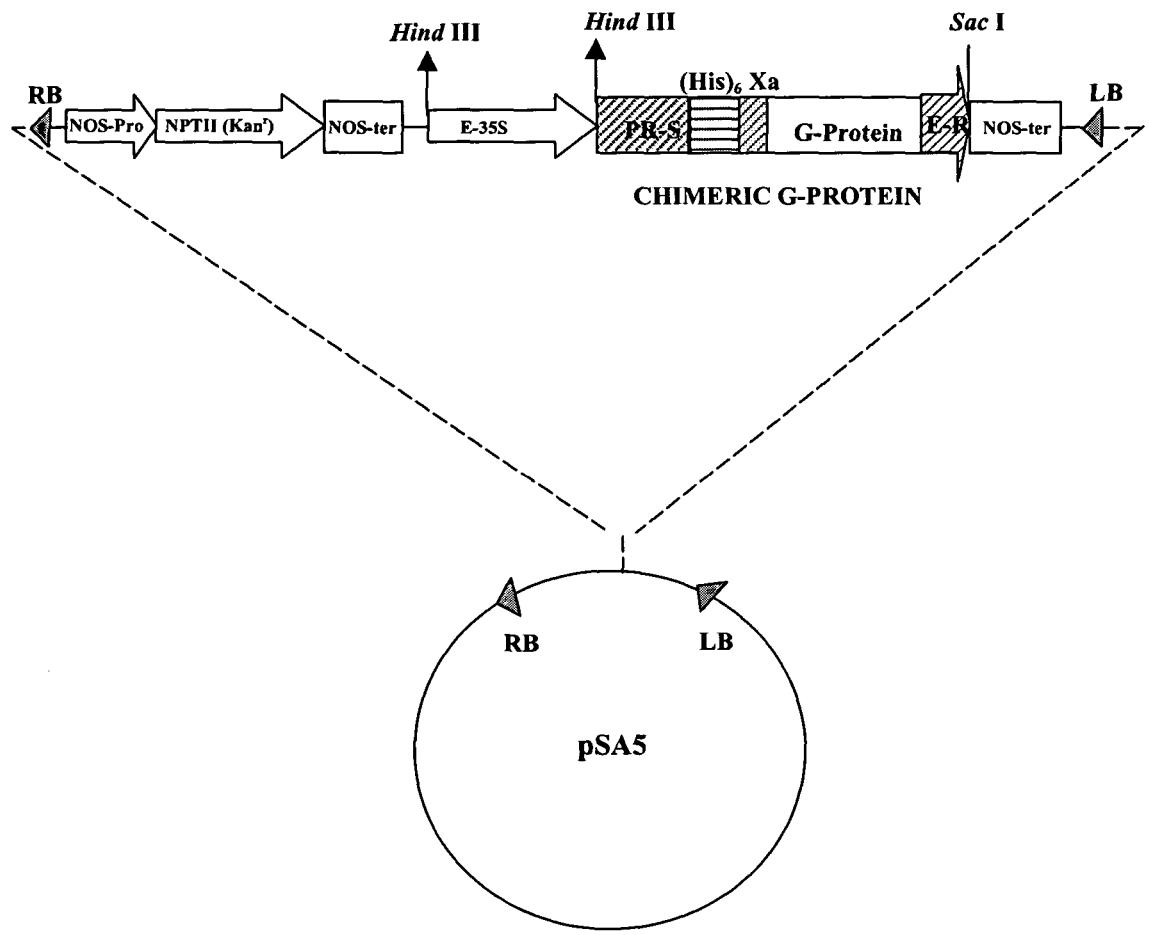
FIG. 5 depicts the plant expression cassette used for developing transgenic plants. (His)$_6$ disclosed as SEQ ID NO: 55.

A plant transformation vector was constructed for the development of transgenic plants. A plasmid pPK201 (having CaMV35S promoter with duplicated enhancer) was digested with HindIII to excise out CaMV35S promoter with the duplicated enhancer. The plasmid pSA17 (FIG. 3) was restricted digested with HindIII and SacI to exise the chimeric gene. A triple ligation was carried for cloning of the two above said fragments in pBI 101 binary vector (New England Biolabs). The resultant plasmid, namely pSA5 (FIG. 5) had CaMV35S promoter with the duplicated enhancer at the upstream of the chimeric gene and nos transcription terminator at the downstream of chimeric gene. Correct orientation of CaMV35S with the duplicate enchancer promoter to chimeric gene was checked by restriction digestion by PstI restriction enzyme. The nos transcription terminator was cloned at the downstream of the chimeric gene. The expression cassette consisting of the synthetic gene with CaMV35S with the duplicate enchancer promoter was cloned in Ti binary vector. The HindIII-HindIII fragment of CaMV35S with the duplicate enchancer promoter was excised from clone pPK201 and HindIII-SacI fragment of chimeric G-protein was excised from clone pSA17 and the two fragments were triple ligated to Ti binary vector pBI 101 at HindIII-SacI site, replacing fragment HindIII-SacI (uidA gene) of the plasmid. This binary vector was named as pSA5. In order to study the efficacy of the chimeric G protein in plants, tobacco was selected for the expression. Agrobacterium tumefaciens strain LBA4404 (pAL4404) was transformed with the binary vector pSA5 following the modified protocol of "electroporation of Agrobacterium" discussed by Cangelosi et al. (1991) and transformed colonies were selected on antibiotics streptomycin, rifampicin and kanamycin. Agrobacterium mediated transformation of Nicotiana tabacum cv. Patit Havana was carried out following the method of Horsch et al., 1985 and the transgenic plant were selected on the antibiotic kanamycin. The presence of the gene encoding chimeric G protein was confirmed with PCR and Southern analysis and the expression of the transgene was established with the RT-PCR, and transcript level was analysed by real time PCR using ABI PRISM 7700 Sequence Detection System (Applied Biosystem), Western analysis and ELISA. Western analysis displayed 0.2% expression of the chimeric protein out of total soluble leaf protein in a selected transgenic line. Such high level of the expression achieved in this study was in contrast to the earlier mentioned report by McGarvey et al (1995). This was the result of designing a novel synthetic gene in which several aspects related to achieving high level expression in plants were exclusively used. Plant preferred translation initiation context, the codons, gene sequence, signal sequence etc. used in this study would have played important role in achieving enhanced expression in plant leaves. In this respect the present gene and the construct are novel.

The following examples are given by way of illustrations and therefore should not be construed to limit the scope of the present invention.

EXAMPLE 1

Expression of the chimeric gene in *Escherichia coli*

A gene coding for the chimeric G protein of 547 amino acid residues length, herein said chimeric G protein was strategically designed (SEQ ID NO. 1). The native polypeptide domain (from position 1 to 19) of G protein was replaced with PR-S signal peptide of tobacco (from position 1 to 26). Following that, a hexapeptide of histidine amino acid (SEQ ID NO: 55) a residues and tetrapeptide comprising the amino acid residues IEGR (SEQ ID NO: 61) were included at the N-terminus of the gene in that order. Following the G protein coding sequence, a hexapeptide coding for SEKDEL (SEQ ID NO: 59) for retention of the chimeric G protein in endoplasmic reticulum was included at the C-terminus extreme of the chimeric gene (SEQ ID NO. 1). A 1.67 kb nucleotide sequence was theoretically designed (SEQ ID NO. 2) to code for the above-mentioned chimeric G protein. Several 6-base cutter restriction enzyme sites were created in the designed gene. HindIII and SalI restriction sites were created at 5'-end and BamHI ,SacI at the 3'-end of the designed gene. The gene was divided into 50 overlapping oligonucleotides (40 to 58 nucleotides long). Each oligonucleotide had 13-18 nucleotide long overlap with the immediately adjacent oligonucleotides on the complementary strand ($T_m$ between 48-50° C.). Oligonucleotides were synthesized on a DNA synthesizer (Gene Assembler Special, Pharmacia, Sweden) at 200 nmole scale and purified on denaturing urea-PAGE. All 50 oligonucleotides were assembled into the double-stranded DNA, herein said chimeric G gene following the ligation-free gene synthesis method of Singh et al. (1996). The DNA was digested with HindIII and SacI restriction enzyme and cloned in pBluescriptII SK(+) (Stratagene). The plasmid was named as pSA17 (shown in FIG. 3). The nucleotide sequence of the synthetic DNA was confirmed by sequencing the cloned synthetic DNA on automated DNA sequencing system (Applied Biosystems model 377). The nucleotide sequence of the synthetic gene designed in this study is novel and differs substantially (FIG. 1) from the gene sequence reported earlier.

A cassette was constructed for the expression of the chimeric toxin in *E.coli* under control of T7 lac promoter. For this purpose, the plasmid pSA17 was amplified by two primers to create NdeI and BamHI sites at the upstream and downstream of the amplicon and cloned in expression vector pET-19b (Novagen)at the same sites. The plasmid was named as PSA33 (shown in FIG. 4). DNA encoding the mature chimeric G protein with factor Xa cleavage site with vector encoded ten histidine residue long tag (SEQ ID NO: 62) followed by enterokinase site at the upstream of chimeric G protein *E. coli* BL21DE3 was transformed with the construct pSA33. The chimeric G protein was expressed by induction with IPTG.

The expression was carried out at 37° C. for different periods. *E.coli* cells were lysed in SDS PAGE loading buffer and resolved on 10% denaturing gel. The result of SDS PAGE and western show that E.coli expressed the recombinant protein of expected size 60.65 kDa which is comparable to that of molecular weight determined by a protein molecular weight analysis program of non glycosylated modified protein which hereby confirmed that the synthetic gene, herein said the gene for chimeric G-protein was developed and expressed correctly. The amino acid sequence of the chimeric G-protein designed for expression in *E. coli* and plants is novel and differs substantially (FIG. 2) from the protein sequence reported earlier.

EXAMPLE 2

Immunization of BalbC mice with plant derived vaccine.

In order to establish efficacy of the novel chimeric G-protein in plants, a plant transformation vector was constructed for the development of transgenic plants.

A plasmid pPK201 (having CaMV35S promoter with duplicated enhancer) was digested with HindIII to excise out CaMV35S promoter with the duplicated enhancer. The plasmid pSA17, containing the chimeric G-protein gene cloned at HindIII-SacI in Bluescript II SK+(Stratagene, La Jolla, Calif.) was prepared as described in Example 1. The chimeric gene consists of 26 amino acid residues of PRS signal peptide of tobacco followed by six histidine residues (SEQ ID NO: 55), four amino acid residues for factor Xa cleavage site, 505 amino acid residues of matured ERA rabies Glycoprotein and six amino acid residues for endoplasmic reticulum retention signal at C' terminus of the chimeric G-protein gene in that order (SEQ ID NO. 1). A 1.67 Kb, sequence was theoretically designed using plant preferred codons to achieve high level expression of the above mentioned chimeric G-protein. A novel translational initiation context (TAAACAATGAAC (SEQ ID NO: 60)) was included at 5' extreme and two stop codons TGA,TGA were introduced at the end of the reading frame of the chimeric G protein. The gene was divided into 50 overlapping oligonucleotides and assembled into 1.67 kb double stranded DNA, following ligation free gene synthesis method of Singh et al. (1996). HindIII and XbaI restriction sites were created at the upstream and BamHI and SacI at the downstream of the gene to facilitate cloning. The chimeric G protein was cloned at HindIII-SacI restriction sites of Bluescript II SK+, sequenced and named as pSA17. The clone pSA17 was digested by HindIII and SacI to excise the 1.67 kb fragment having a complete chimeric G-protein gene (SEQ ID NO. 2). A triple ligation was carried out for the cloning of the two fragments, that is, the HindIII fragment of clone pPK201 (having CaMV35S promoter with duplicate enhancer) and HindIII-SacI fragment having a chimeric gene. The resultant clone was name as pSA17. The above two fragments were triple ligated to pBI101 at HindIII-SacI, replacing the (-glucuronidase cassette. The plant expression cassette had a CaMV35S promoter with the duplicated enhancer at the upstream of the chimeric gene and 260 by fragment containing the polyadenylation signal from the nopaline synthase gene (Nos-ter) transcription terminator at the downstream of the chimeric gene. The expression cassette had the NPTII gene for kanamycin resistance under the control of Nos promoter. The correct orientation of CaMV35S with duplicate enhancer was confirmed by restriction analysis. The expression cassette (the synthetic chimeric-G protein gene with E-35S promoter) cloned in Ti binary vector HindIII-SacI of pBI101 with correct orientation of E-35S to chimeric-G protein was named as pSA5 (shown in FIG.5). The construct had polynucleotide sequences TAAACAATG AAC (SEQ ID NO: 60) as plant preferred translation initiation context. Two stop codons TGA, TGA were introduced in synthetic gene for translational termination. *Agrobacterium tumefaciens* strain LBA 4404 (pAL4404) was transformed with binary vector pSA5 following the modified protocol of "electroporation of *Agrobacterium*" discussed by Cangelosi et al. (1991) and transformed colony was selected on antibiotics streptomycin, rifampicin and kanamycin. *Agrobacterium* mediated transformation of *Nicotiana tabacum* cv. Patit Havana was carried out following the method of Horsch et al., 1985 and the transgenic plant were selected on the antibiotic kanamycin. The presence of the gene encoding chimeric G-protein was confirmed with PCR and Southern analysis and the expression of the transgene was established with the RT-PCR, Real Time PCR, Western analysis and ELISA. Western result established expression of the toxin protein at 0.2% of soluble leaf protein in the transgenic line selected for these experiments. Such a high level of the expression substantiates the novel designing of the gene in which plant-preferred codons, preferred translation initiation context, endoplasmic reticulum retention signal selected by us and other features of the gene sequence designed by us play an important role in the expression. Chimeric G-protein was partially purified from the leaves of tobacco plants expressing the synthetic gene at a high leve1. 100 gm of fresh leaves of tobacco were washed, frozen in liquid nitrogen, ground with mortar and pestle and homogenized in a Polytron blender in ice cold extraction buffer {100 mM Tris-HCl pH 8.0, 150 Mm NaCl, 150 mM sorbitol, 2 mM DTT, 0.1% deica, 1 mM PMSF, 0.1% leupeptin, 2% polyvinylpolypyrrolidone, 0.05% plant protease inhibitor cocktail (sigma)}. Leaf tissue was homogenized in 3 ml/gm of the extraction buffer. After homogenization, the mixture was filtered through a layer of nylon mesh and centrifuged at 1800 xg for 5 min at 4° C. The supernatant promoter. The correct orientation of CaMV35S with duplicate enhancer was confirmed by restriction analysis. The expression cassette (the synthetic chimeric-G protein gene with E-35S promoter) cloned in Ti binary vector HindIII-SacI of pBI101 with correct orientation of E-35S to chimeric-G protein was named as pSA5 (shown in FIG.5). The construct had polynucleotide sequences TAAACAATG AAC (SEQ ID NO: 60) as plant preferred translation initiation context. Two stop codons TGA, TGA were introduced in synthetic gene for translational termination. *Agrobacterium tumefaciens* strain LBA 4404 (pAL4404) was transformed with binary vector pSA5 following the modified protocol of "electroporation of *Agrobacterium*" discussed by Cangelosi et al. (1991) and transformed colony was selected on antibiotics streptomycin, rifampicin and kanamycin. *Agrobacterium* mediated transformation of *Nicotiana tabacum* cv. Patit Havana was carried out following the method of Horsch et al., 1985 and the transgenic plant were selected on the antibiotic kanamycin. The presence of the gene encoding chimeric G-protein was confirmed with PCR and Southern analysis and the expression of the transgene was established with the RT-PCR, Real Time PCR, Western analysis and ELISA. Western result established expression of the toxin protein at 0.2% of soluble leaf protein in the transgenic line selected for these experiments. Such a high level of the expression substantiates the novel designing of the gene in which plant-preferred codons, preferred translation initiation context, endoplasmic reticulum retention signal selected by us and other features of the gene sequence designed by us play an important role in the expression. Chimeric G-protein was partially purified from the leaves of tobacco plants expressing the synthetic gene at a high level. 100 gm of fresh leaves of tobacco were washed, frozen in liquid nitrogen, ground with mortar and pestle and homogenized in a Polytron blender in ice cold extraction buffer {100 mM Tris-HCl pH 8.0, 150 Mm NaCl, 150 mM sorbitol, 2 mM DTT, 0.1% deica, 1 mM PMSF, 0.1% leupeptin, 2% polyvinylpolypyrrolidone, 0.05% plant protease inhibitor cocktail (sigma)}. Leaf tissue was homogenized in 3 ml/gm of the extraction buffer. After homogenization, the mixture was filtered through a layer of nylon mesh and centrifuged at 1800 xg for 5 min at 4° C. The supernatant was recentrifuged at 38000 xg for 1 hr, at 4° C. The supernatant was separated and the pellet was solubilized in buffer containing 50 mM Tris pH 8.0, 2 Mm DTT, 2.5% glycerol, 1 Mm PMSF, 0.05% PPIC(plant protease inhibitor cocktail), 1% sodium deoxycholic acid for 1 hr on ice and centrifuged at 38000 xg for 1 hr at 4° C. The supernatant was loaded on ion exchange column sepharose Q fast flow, column was washed with low salt buffer (50 mM tris pH 8, 0.1% triton X100, 0.1% BME), the bound protein was eluted by linear gradient of NaCl. The ELISA positive fractions were pooled and loaded on antibody affinity column {antirabies human IgG linked to CNBr-activated Sepharose 4B(Pharmacia Biotech)}. ELISA positive fractions were collected and the protein was quantitated by Bradford dye (Biorad) taking BSA as a standard and size of the protein was checked by western using antirabies equine IgG antibody. Balb C mice were primed by injecting 25(g each of the membrane protein, in one set and commercially available killed rabies virus vaccine (as a positive control) which was Rabipur, manufactured by Aventis Pharma Ltd. and phosphate buffer saline (as a negative control). Three booster injections were given on the $7^{th}$, $14^{th}$ and $28^{th}$ day. Serum was collected 7 days after the second and third booster. Antibody titer was checked by ELISA (Table 5). These show that plant membrane protein elicits high level of immune response in mice. It is 2-3 fold more immunogenic as compared to commercially available killed rabies virus vaccine.

TABLE 5

| | Total no. of mice injected | Antibody titre after $II^{nd}$ booster | Antibody titre after $III^{rd}$ booster |
|---|---|---|---|
| Pre immune sera | | 0.03 | 0.03 |
| Control mice only PBS | 4 | 0.04 ± 0.007 | 0.139 ± 0.004 |
| Transgenic plant derived membrane fraction enriched with G-protein | 4 | 0.365 ± 0.20 | 0.833 ± 0.20 |
| Commercially available vaccine (inactivated virus by Aventis Pharma Ltd.) | 5 | 0.097 ± 0.009 | 0.241 ± 0.01 |

EXAMPLE 3

Immunoprotection Analysis of Immunized Mice

The efficacy of plant derived G protein was studied in immunoprotection by injecting the G enriched plant membrane fraction in mice and challenging it with live rabies virus. Mice were intraperitoneally injected by the G protein enriched membrane fraction of transgenic tobacco leaves and a commercially available killed rabies virus vaccine (as positive control Rabipur by Aventis Pharma Ltd.) and phosphate buffer saline (as negative control). As described in Example 2, boosters were given on 7, 14 and $28^{th}$ day. At each stage a total of 25 μg of protein was injected. After the third booster, mice were intracerebrally challenged with $10 \times LD_{50}$ of live rabies virus and observed for the appearance of symptoms. After thirteen days of the challenge the result was noted down and are shown in the table 6 and FIG. 7.

TABLE 6

| | Total no. of mice | Mice survived | % Protection |
|---|---|---|---|
| Control mice | 6 | 0 | 0 |
| Plant derived membrane fraction enriched with G protein | 3 | 3 | 100% |
| Commercially available vaccine (inactivated virus by Aventis Pharma Ltd.) | 2 | 2 | 100% |

The results obtained after the challenge experiment clearly show that the G protein located in plant cell membrane elicits a high level of immune response and is highly immunoprotective.

Thus, the present invention provides, inter alia, a very safe vaccine as compared to inactivated virus for rabies management in human, pets and wild life. It does not require handling of a live pathogenic virus and has no risk of vaccine reverting to infective virus particles.

G-protein of rabies virus was designed theoretically to express at high level in novel hosts, including transgenic plants and plant cell lines, microbes like E. coli and yeast and animals and animal cell lines recombinant animal and plant viruses. Thus, without handling a pathogenic virus, as this an immunogenic antigen can be produced in new host cells. Chimeric G-protein was designed specifically to express at high level in plants cells. With a suitable signal peptide the G protein was made to accumulate in membranes of plant cells. Comparable signals can be used to accumulate in specific compartments. Enrichment of target protein in specific organelle like membrane allows the development of less expensive and convenient approaches for large scale preparation of the target protein in animal cell lines and yeast.

Hexa-histidine tag (SEQ ID NO: 55) was designed at N-terminus extreme to further facilitate purification of chimeric protein on immobilized metal affinity column. Since monospecific antibody against histidine tag is commercially available, the histidine tag can also be used for the identification the tagged chimeric protein during various stages of purification. Factor Xa cleavage site was included at the downstream of histidine tag to chop it off after purification, in case this is not desired in therapeutic applications. SEKDEL (SEQ ID NO: 59) retention signal was designed at the C-terminus extreme which enhanced the accumulation of chimeric G-protein in endoplasmic reticulum of cell. Compartmentalization of heterologous proteins in endoplasmic reticulum can enhance their stability and overall accumulation. This makes the purification procedure simpler and efficient. Further, membrane localization prevents the target protein from proteolytic enzymes present in cytosol. Also membrane localization can lead to functionally important modifications in the target protein.

The immune response elicited with the chimeric G-protein was several folds higher as compared to the commercially available inactivated rabies virus vaccine. The immunised animals exhibited immunoprotection against live virus challenge. High immune response of G protein localized in tobacco leaf membranes reflects novel designing of the protein since it allows the G protein to take an immunologically active conformation.

Employment of chimeric G-protein purified from plants for rabies management will be very safe as the vaccine preparations will be free of animal pathogens, like HIV, Fowlpox, Madcow, prions etc.

Chimeric G-protein can be used as an oral vaccine, if it is expressed in edible parts of the plants like leaves, grains etc. Rabies virus has earlier been shown to be immuno stimulatory/immunoprotective when given orally to experimental animals. Hence expressing functionally active rabies capsid G-protein in plant leaves opens new opportunities of developing an inexpensive vaccine that is expected to be safe and does not require cold chain, if transported in form of seeds, grain, plant storage tissue etc.

We claim:

1. A recombinant chimeric glycoprotein (G-protein) comprising SEQ ID No. 1.

2. The recombinant chimeric G-protein of claim 1, wherein the length of the protein comprises 547 amino acids.

3. The recombinant chimeric G-protein of claim 1, wherein from N to C terminal, the protein comprises the following: amino acids 1-26 comprise a pathogen-related protein S (PR-S) signal peptide, amino acids 27-32 comprise a hexa-histidine tag (SEQ ID NO: 55), amino acids 33-36 are a tetrapeptide factor Xa proteolytic cleavage site, amino acids 37-541 comprise a mature glycoprotein G of ERA strain of rabies virus and amino acids 542-547 provide for compartmentalization of the chimeric protein in endoplasmic reticulum.

4. A recombinant chimeric G-protein based rabies vaccine comprising SEQ ID No. 1.

5. The rabies vaccine of claim 4, wherein length of protein comprises 547 amino acids.

6. The rabies vaccine of claim 4, wherein from N to C terminal, the protein comprises the following: amino acids 1-26 comprise a PR-S signal peptide, amino acids 27-32 comprise a hexa-histidine tag (SEQ ID NO: 55), amino acids 33-36 are a tetrapeptide factor Xa proteolytic cleavage site, amino acids 37-541 comprise a mature glycoprotein G of ERA strain of rabies virus and amino acids 542-547 provide for compartmentalization of the chimeric protein in endoplasmic reticulum.

7. The rabies vaccine of claim 4, wherein recombinant chimeric G-protein gene encodes a protein having immunoprotective activity against live rabies virus.

8. The rabies vaccine of claim 4, wherein the vaccine provides 100% immunoprotection against rabies virus.

9. The rabies vaccine of claim 4, wherein the vaccine controls rabies in humans, pets and wild life.

10. A recombinant nucleic acid sequence of SEQ ID No 2, wherein the nucleic acid sequence construct encodes the chimeric G-protein of claim 1.

11. The recombinant nucleic acid sequence of claim 10, wherein the recombinant nucleic acid sequence is of length 1.67 kb.

12. A method for large scale production of a rabies vaccine comprising a chimeric G protein of SEQ ID No. 1 in plants, said process comprising:
   a. transforming a plant with a DNA molecule of SEQ ID No. 2 that encodes the chimeric G protein of SEQ ID No. 1 under conditions whereby the DNA is expressed and the chimeric G protein is produced and localized in the endoplasmic reticulum of the plant, and
   b. isolating and purifying the chimeric G protein for immunization of a suitable subject.

13. The method of claim 12, wherein the commercially available strain of rabies virus is selected from the group consisting of ERA strain and CVS strain.

14. The method of claim 12, wherein the chimeric protein is of length 547 amino acids.

15. The method of claim 12, wherein the recombinant recombinant nucleic acid sequence gene encodes a chimeric protein having immunoprotective activity against live rabies virus.

16. The method of claim 12, wherein the vaccine controls rabies in humans, pets and wild life.

17. The method of claim 12, wherein the plant for expressing recombinant G-protein gene is selected form the group consisting of tobacco, corn, chickpea, pigeonpea, groundnut, soybean, tomato, potato, musk melon, water melon, spinach, cauliflower, cabbage, chili, capsicum, carrot, and algae.

18. The method of claim 12, wherein the protein is 2-4 folds more immunogenic as compared to inactivated virus.

19. The method of claim 12, wherein the vaccine expression is about 0.2% of total soluble protein in plant.

20. A method of immunizing a subject against rabies, comprising administering to said subject a recombinant chimeric G-protein having SEQ ID No. 1, wherein the vaccine is produced and expressed in transgenic plants admixed with a carrier in an amount effective to protect the subject against rabies.

21. The method of claim 20, wherein the subject is selected from the group consisting of human, pets and wild life.

22. The method of claim 20, wherein the administration is through the routes selected from oral, intraperitoneally etc.

23. The method of claim 20, wherein the recombinant chimeric G-protein gene vaccine is of concentration ranging of at least nanogram.

24. The method of claim 20, wherein the vaccine is safe for the administration.

25. The method of claim 20, wherein the vaccine is stable for years as in seeds, tubers, roots, leaves and other plant parts.

26. The method of claim 20, wherein the antibody titre of the said protein is in the range of 0.365±0.20 after the second booster dose and 0.833±0.20 after the third booster dose.

27. The method of claim 20, wherein the said vaccine provides 100% immunoprotection.

* * * * *

UNITED STATES PATENT AND TRADEMARK OFFICE
CERTIFICATE OF CORRECTION

PATENT NO. : 7,901,691 B2  
APPLICATION NO. : 11/202864  
DATED : March 8, 2011  
INVENTOR(S) : Rakesh Tuli et al.

Page 1 of 1

It is certified that error appears in the above-identified patent and that said Letters Patent is hereby corrected as shown below:

Title Page:

In (73) Please correct the Assignee Information As Follows:

(73) Assignees: Council of Scientific and Industrial Research, New Delhi (IN);

Unichem Laboratories Ltd., Mumbai (IN);

Indian Veterinary Research Institute, Izatnagar (IN)

Signed and Sealed this
Twenty-sixth Day of April, 2011

David J. Kappos
*Director of the United States Patent and Trademark Office*